United States Patent
Harada et al.

(10) Patent No.: US 11,389,054 B2
(45) Date of Patent: Jul. 19, 2022

(54) ENDOSCOPE, WIRE ATTACHING METHOD FOR ENDOSCOPE, AND WIRE DETACHING METHOD FOR ENDOSCOPE

(71) Applicant: FUJIFILM Corporation, Tokyo (JP)

(72) Inventors: Takashi Harada, Kanagawa (JP); Takuro Asaoka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 641 days.

(21) Appl. No.: 16/392,551

(22) Filed: Apr. 23, 2019

(65) Prior Publication Data

US 2019/0246886 A1    Aug. 15, 2019

Related U.S. Application Data

(63) Continuation of application No. PCT/JP2017/031953, filed on Sep. 5, 2017.

(30) Foreign Application Priority Data

Nov. 30, 2016    (JP) .............................. JP2016-233154

(51) Int. Cl.
  *A61B 1/00*    (2006.01)
  *A61B 1/018*    (2006.01)
  (Continued)

(52) U.S. Cl.
  CPC ............ *A61B 1/018* (2013.01); *A61B 1/0011* (2013.01); *A61B 1/00128* (2013.01);
  (Continued)

(58) Field of Classification Search
  None
  See application file for complete search history.

(56) References Cited

U.S. PATENT DOCUMENTS

| 5,562,600 A | 10/1996 | Matsuno |
| 2001/0044570 A1* | 11/2001 | Ouchi ................ A61B 1/00177 600/107 |

(Continued)

FOREIGN PATENT DOCUMENTS

| EP | 2878272 | 6/2015 |
| JP | S60220031 | 11/1985 |

(Continued)

OTHER PUBLICATIONS

"International Search Report (Form PCT/ISA/210) of PCT/JP2017/031953," dated Nov. 21, 2017, with English translation thereof, pp. 1-3.

(Continued)

*Primary Examiner* — Timothy J Neal
(74) *Attorney, Agent, or Firm* — JCIPRNET

(57) ABSTRACT

According to a endoscope, an engaging part delivered from a delivery port advances while being guided to an opening of a housing part by an engagement guide path. Then, as the engaging part comes into contact with a deformation generating part, the engaging part is moved in a direction from a bottom surface of the housing part toward the opening, and thereby, the wire is elastically deformed. Then, in a case where the engaging part that advances within the engagement guide path has passed by the deformation generating part, the engaging part is housed in the housing part from the opening by a restoring force of the wire.

16 Claims, 25 Drawing Sheets

(51) Int. Cl.
   *A61B 1/273* (2006.01)
   *A61B 1/12* (2006.01)
(52) U.S. Cl.
   CPC ............ *A61B 1/00177* (2013.01); *A61B 1/12* (2013.01); *A61B 1/273* (2013.01)

(56) References Cited

U.S. PATENT DOCUMENTS

2012/0078041 A1* 3/2012 Kitano ............... A61B 1/00098
                                                        600/107
2016/0270633 A1   9/2016 Iwasaka et al.

FOREIGN PATENT DOCUMENTS

| JP | H05253177 | 10/1993 |
| JP | H06315458 | 11/1994 |
| JP | 3302096 | 7/2002 |
| JP | 2015165839 | 9/2015 |

OTHER PUBLICATIONS

"Written Opinion of the International Searching Authority (Form PCT/ISA/237) of PCT/JP2017/031953," dated Nov. 21, 2017, with English translation thereof, pp. 1-7.
"Search Report of Europe Counterpart Application", dated Nov. 15, 2019, p. 1-p. 5.

* cited by examiner

FIG. 7
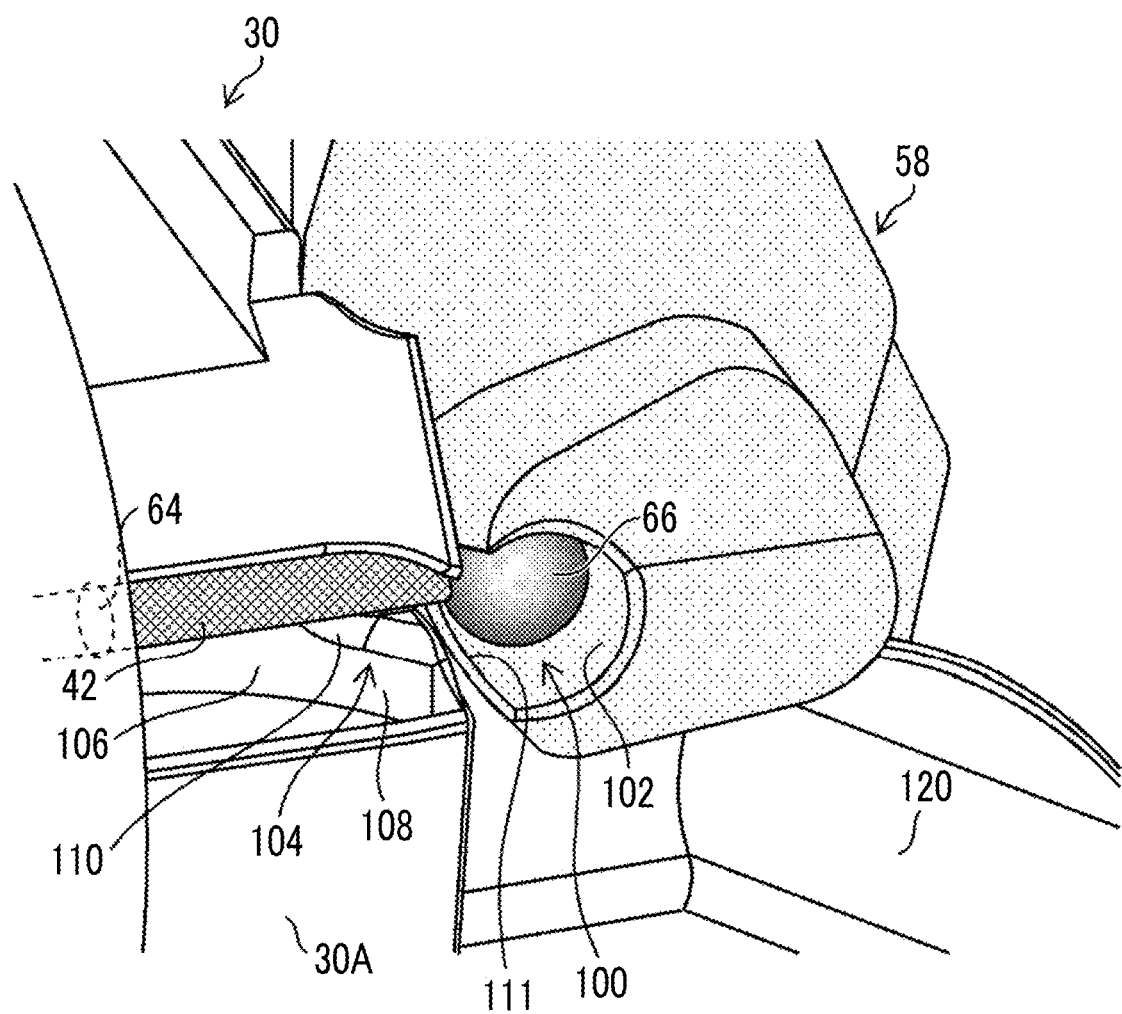
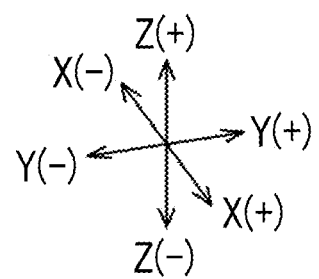

FIG. 12
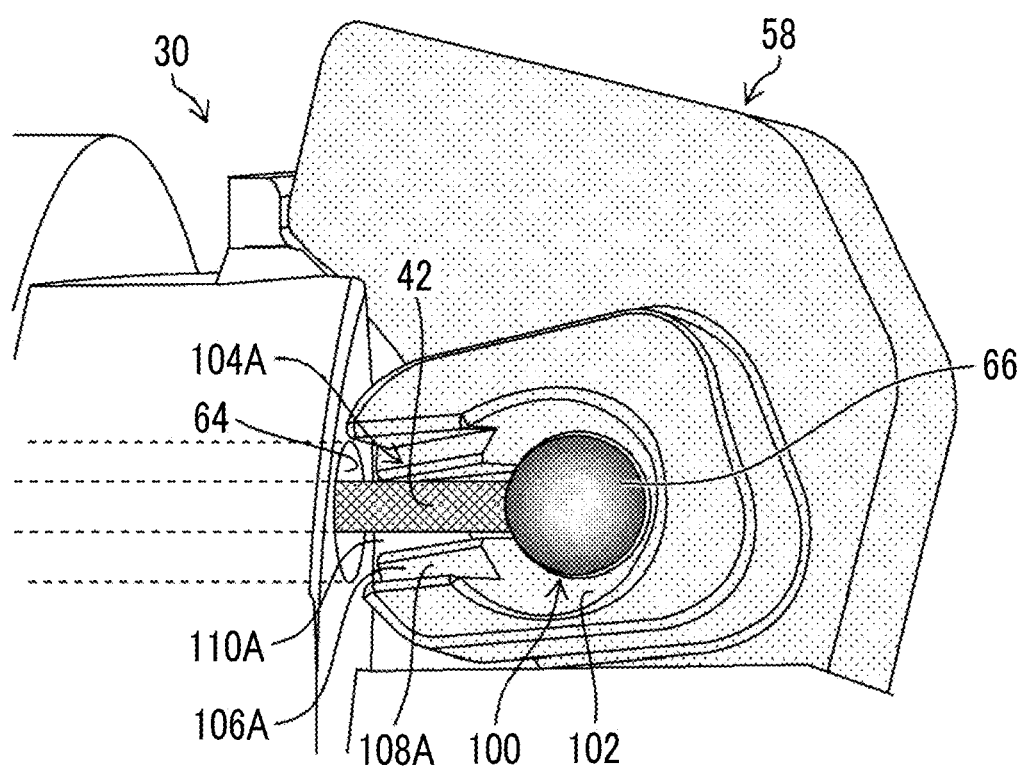
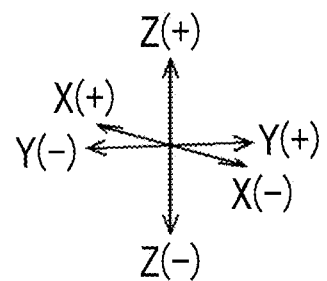

FIG. 16
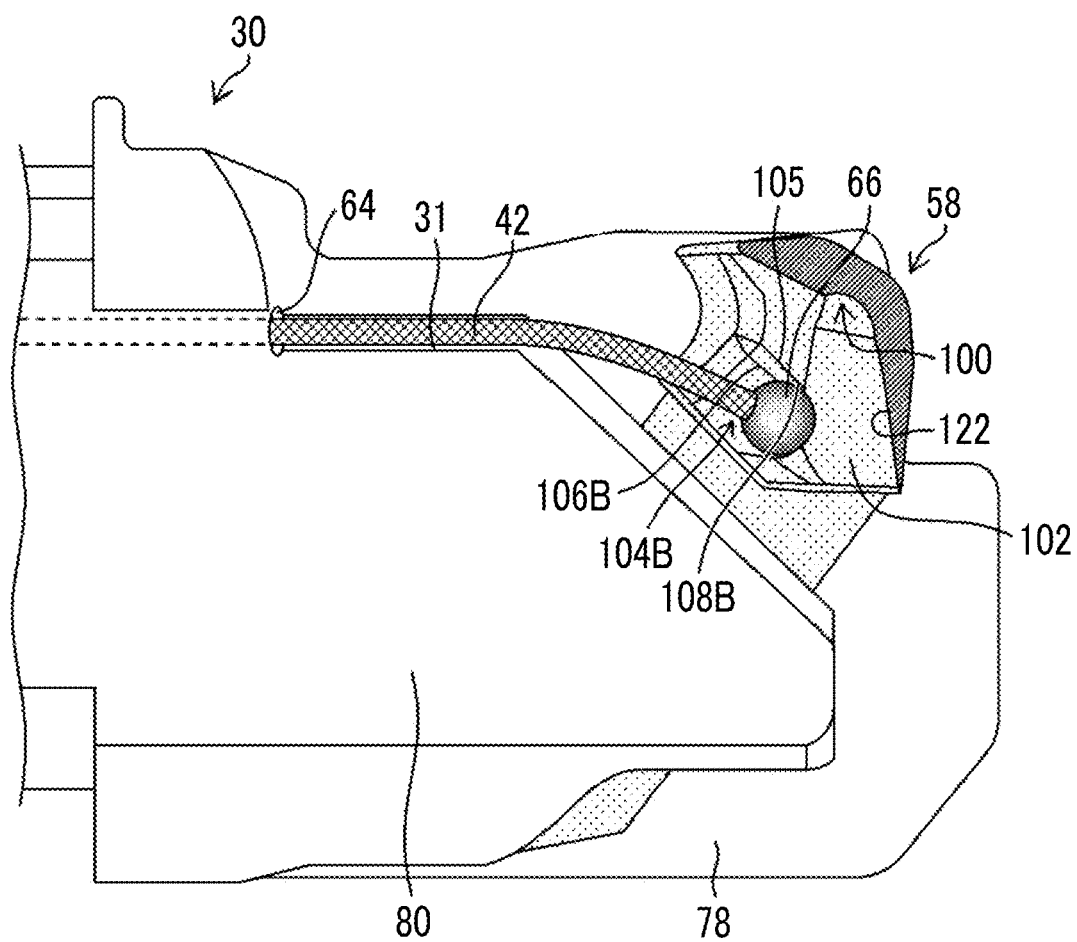
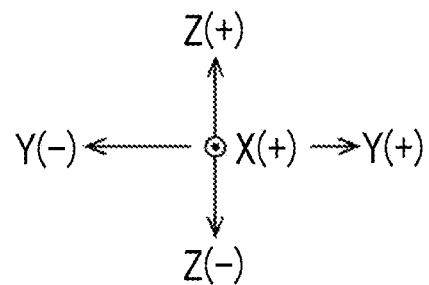

FIG. 19
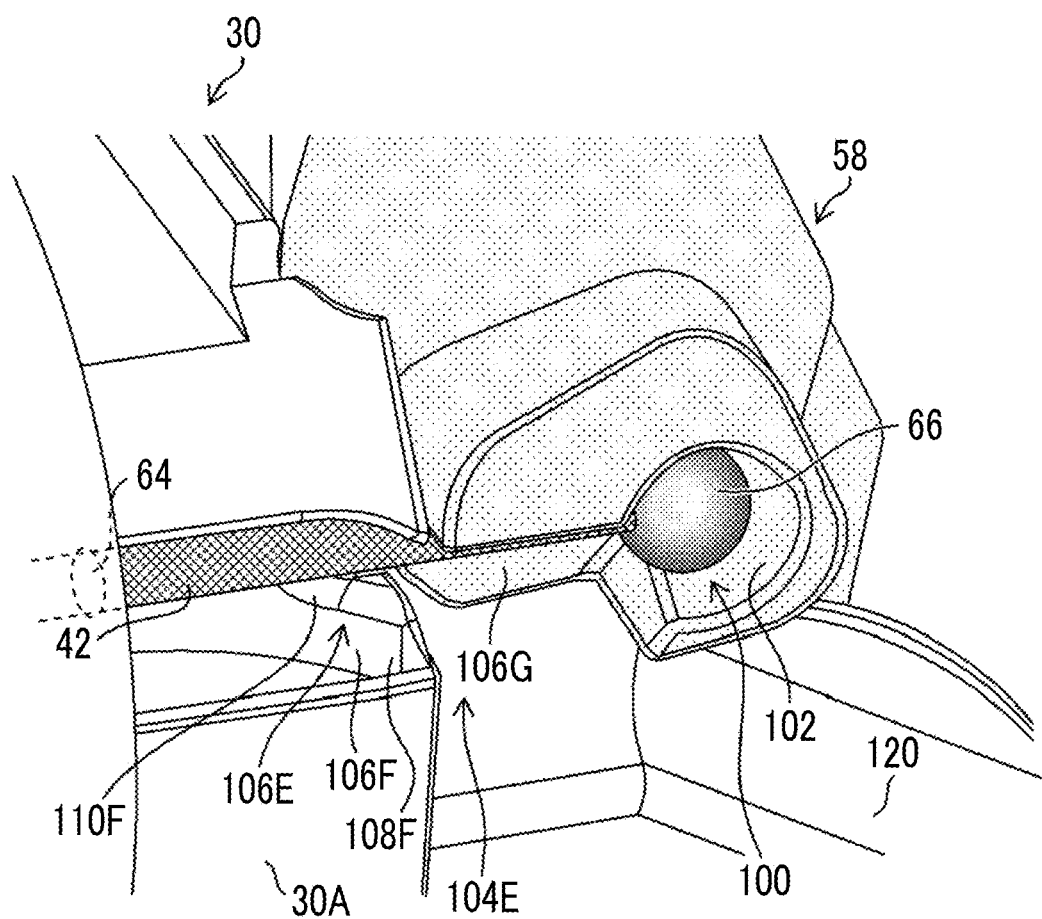
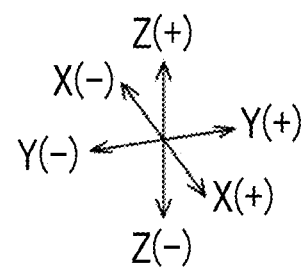

FIG. 20
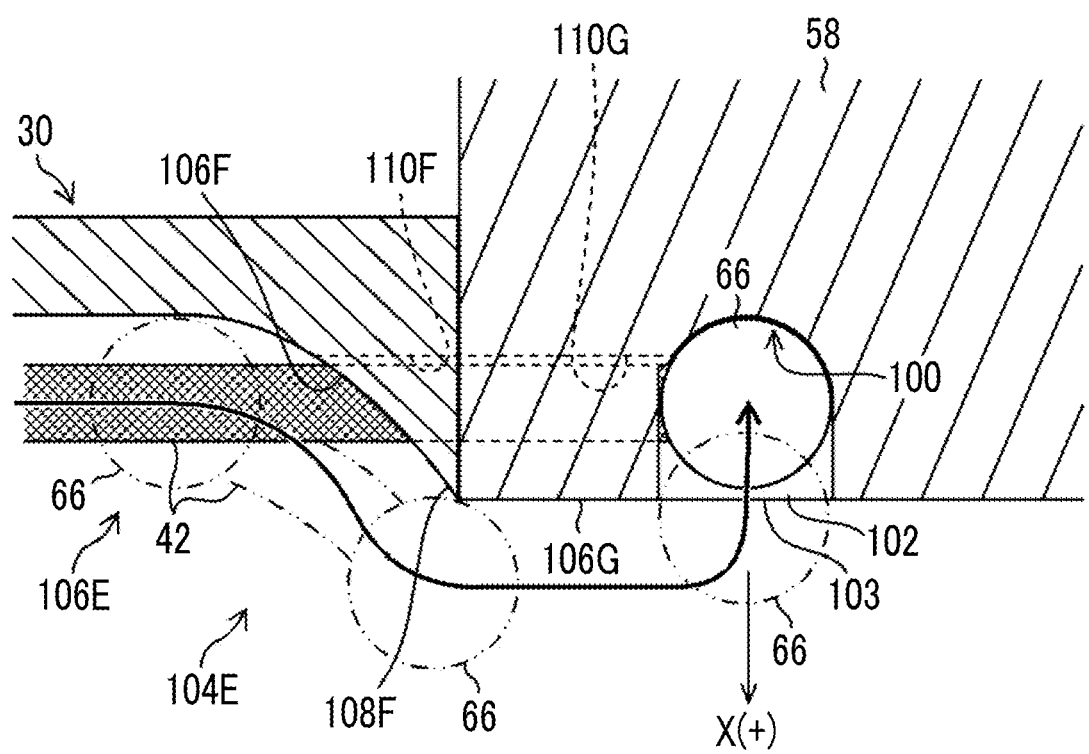
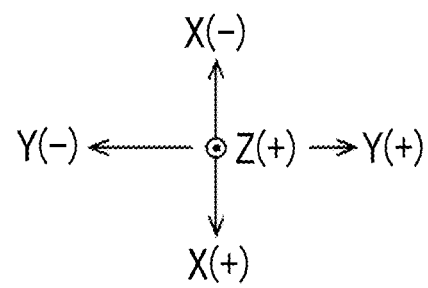

ENDOSCOPE, WIRE ATTACHING METHOD FOR ENDOSCOPE, AND WIRE DETACHING METHOD FOR ENDOSCOPE

CROSS-REFERENCE TO RELATED APPLICATIONS

This application is a Continuation of PCT International Application No. PCT/JP2017/031953 filed on Sep. 5, 2017, which claims priority under 35 U.S.C. § 119(a) to Japanese Patent Application No. 2016-233154 filed on Nov. 30, 2016. Each of the above application(s) is hereby expressly incorporated by reference, in its entirety, into the present application.

BACKGROUND OF THE INVENTION

1. Field of the Invention

The present invention relates to an endoscope, a wire attaching method for an endoscope, and a wire detaching method for an endoscope, and particularly to an endoscope comprising a treatment tool erection pedestal for changing the delivery direction of a treatment tool at a distal end part of an insertion part, a wire attaching method for an endoscope, and a wire detaching method for an endoscope.

2. Description of the Related Art

In endoscopes, various treatment tools are inserted from a treatment tool introduction port provided in a proximal operating part (hereinafter referred to as an "operating part"), and the treatment tools are delivered from a treatment tool delivery port opening to a distal end member of an insertion part to the outside, and are used for treatment. For example, treatment tools, such as forceps or an imaging tube, are used in duodenum mirrors, and treatment tools, such as a puncturing needle, are used in ultrasonic endoscopes. In such treatment tools, it is necessary to change a delivery direction in a distal end member, in order to treat a desired position within a subject. For this reason, the distal end member is provided with a treatment tool erection pedestal (also referred to as a forceps erection pedestal; hereinafter, referred to an "erection pedestal"). Additionally, the endoscopes are provided with a treatment tool erection mechanism that changes the posture of the erection pedestal between an erected position and a lodged position.

As the treatment tool erection mechanism, a wire pulling type mechanism to which a distal end part of a wire is directly attached to the erection pedestal is known (refer to JP1994-315458A (JP-H06-315458A)). This mechanism is a mechanism that a proximal end side of the wire is coupled to an operating lever provided in the operating part, and the posture of the erection pedestal is changed between the erected position and the lodged position by performing a push/pull operation of the wire by the operating lever, thereby rotating the erection pedestal around a rotational movement shaft.

Meanwhile, in a case where an endoscope is used for various kinds of examination or treatment, liquids within a body cavity adhere to the distal end member of the insertion part comprising the erection pedestal, and a guide pipe through which the wire is inserted. Thus, after use, the endoscope is subjected to cleaning and disinfection processing, using a cleaning solution and a disinfection solution. In that case, since the diameter of the guide pipe is small and the wire is inserted through the guide pipe, substantial time and effort are taken for the cleaning.

Thus, in the endoscope of JP1994-315458A (JP-H06-315458A), a cover that covers the distal end member of the insertion part, the erection pedestal, and the wire are attachably and detachably provided, and the cover, the erection pedestal, and the wire are detached to clean the guide pipe of the wire.

Additionally, an example of the endoscope in which the wire is adapted to be capable of being attached to and detached from the erection pedestal is disclosed in JP1994-315458A (JP-H06-315458A). According to this endoscope, a tip is provided at a distal end part of the wire, and the erection pedestal is provided with a housing part that houses the tip.

According to the endoscope of JP1994-315458A (JP-H06-315458A), first, the tip of the wire after use is detached from the tip housing part of the erection pedestal, and next, the wire after use is extracted from the guide pipe. Next, cleaning of the endoscope performed. Thereafter, the distal end part of the wire and the erection pedestal are manually coupled to each other by inserting a new wire through the guide pipe and housing the tip of the distal end part of the wire in the tip housing part of the erection pedestal.

SUMMARY OF THE INVENTION

However, since the distal end member of the insertion part of the endoscope is downsized along with the reduction in diameter of the insertion part, the tip of the wire disclosed in JP1994-315458A (JP-H06-315458A) also has a minute size. There is a problem that it takes substantial time and effort to manually house such a minute chip in the tip housing part of the erection pedestal.

In the endoscope of JP1994-315458A (JP-H06-315458A), the economical effect can be obtained by making only the wire after use replaceable with a new wire. However, there is a problem that substantial time and effort is required for the coupling between a distal end part of the new wire and the erection pedestal.

The invention has been made in view of such circumstances, a first object thereof is to provide an endoscope and a wire attaching method for an endoscope that can easily couple a distal end part of a wire and a treatment tool erection pedestal to each other, and a second aspect thereof is to provide a wire detaching method for an endoscope that can easily detach the distal end part of the wire from the treatment tool erection pedestal.

In order to achieve the first object of the invention, an endoscope related to the invention comprises a proximal operating part including an operating member; an insertion part having a proximal end part connected to the proximal operating part; a distal end member that is provided at a distal end part of the insertion part; a treatment tool erection pedestal that is attached to the distal end member and is rotationally movable between an erected position and a lodged position; a wire that is coupled to the treatment tool erection pedestal on a distal end side thereof, is coupled to the operating member on a proximal end side thereof, and is pushed and pulled depending on an operation of the operating member, thereby rotationally moving the treatment tool erection pedestal; an engaging part that is provided at a distal end part of the wire; a housing part that is provided in the treatment tool erection pedestal and is formed with an opening for housing the engaging part; an introduction port that is provided in the proximal operating part and allows the wire to be introduced thereinto with the engaging part as a head; a delivery port that is provided in the distal end member and allows the wire to be delivered therefrom with the engaging part as a head; a wire insertion channel that is provided inside the insertion part and communicates the introduction port with the delivery port; and an engagement guide part that is installed consecutively with the housing part, is provided in at least one of the distal end member or the treatment tool erection pedestal, and guides the engaging part delivered from the delivery port, to the opening of the housing part.

According to the invention, in a case where the wire is introduced with the engaging part as a head from the introduction port of the proximal operating part, the engaging part passes through the wire insertion channel and is delivered from the delivery port of the distal end member to the outside. Then, the engaging part is guided toward the opening of the housing part of the treatment tool erection pedestal by the engagement guide part by the continued introduction operation of the wire, and is housed in the housing part from the opening. Accordingly, according to the invention, the engaging part of the wire can be housed in the housing part of the treatment tool erection pedestal simply by the introduction operation of the wire. Therefore, the distal end part of the wire and the treatment tool erection pedestal can be easily coupled to each other.

In one aspect of the invention, it is preferable that the engagement guide part includes an engagement guide path that guides the engaging part delivered from the delivery port, to the opening of the housing part in a direction from the delivery port toward the housing part; and a deformation generating part that is installed consecutively with the opening of the housing part inside the engagement guide path and comes into contact with the engaging part that advances toward the opening inside the engagement guide path to elastically deform the wire in a direction in which the engaging part goes from a bottom surface of the housing part toward the opening, and the engaging part that advances within the engagement guide path is housed in the housing part from the opening by a restoring force of the wire in a case where the engaging part has passed by the deformation generating part.

According to the one aspect, the engaging part delivered from the delivery port advances while being guided to the opening of the housing part by the engagement guide path. Then, as the engaging part comes into contact with the deformation generating part, the engaging part is moved in the direction from the bottom surface of the housing part toward the opening, and thereby, the wire is elastically deformed. Then, in a case where the engaging part that advances within the engagement guide path has passed by the deformation generating part, the engaging part is housed in the housing part from the opening by the restoring force of the wire. That is, according to the one aspect of the invention, by providing the engagement guide part with the deformation generating part, the engaging part can be housed in the housing part by utilizing a biasing force that is the restoring force of the wire.

In one aspect of the invention, it is preferable that the engagement guide path and the deformation generating part are provided in the distal end member.

According to the one aspect, the engaging part delivered from the delivery port advances while being guided to the opening of the housing part by the engagement guide path of the distal end member. Then, as the engaging part comes into contact with the deformation generating part of the distal end member, the engaging part is moved in the direction from the bottom surface of the housing part toward the opening, and thereby, the wire is elastically deformed. Then, in a case where the engaging part that advances within the engagement guide path has passed by the deformation generating part, the engaging part is housed in the housing part of the treatment tool erection pedestal via the opening by the restoring force of the wire.

In one aspect of the invention, it is preferable that the engagement guide path and the deformation generating part are provided in the treatment tool erection pedestal.

According to the one aspect, the engaging part delivered from the delivery port advances while being guided to the opening of the housing part by the engagement guide path of the treatment tool erection pedestal. Then, as the engaging part comes into contact with the deformation generating part of the treatment tool erection pedestal, the engaging part is moved in the direction from the bottom surface of the housing part toward the opening, and thereby, the wire is elastically deformed. Then, in a case where the engaging part that advances within the engagement guide path has passed by the deformation generating part, the engaging part is housed in the housing part of the treatment tool erection pedestal via the opening by the restoring force of the wire.

In one aspect of the invention, it is preferable that the engagement guide path has a first engagement guide path provided in the distal end member, and a second engagement guide path that is provided in the treatment tool erection pedestal and is connected to the first engagement guide path, and the deformation generating part is installed consecutively with the opening of the housing part within the second engagement guide path.

According to the one aspect, the engaging part delivered from the delivery port advances while being guided from the first engagement guide path of the distal end member to the opening of the housing part by the second engagement guide path of the treatment tool erection pedestal. Then, as the engaging part comes into contact with the deformation generating part within the second engagement guide path, the engaging part is moved in the direction from the bottom surface of the housing part toward the opening, and thereby, the wire is elastically deformed. Then, in a case where the engaging part that advances within the second engagement guide path has passed by the deformation generating part, the engaging part is housed in the housing part of the treatment tool erection pedestal via the opening by the restoring force of the wire.

In one aspect of the invention, it is preferable that the engagement guide part includes an engagement guide path that guides the engaging part delivered from the delivery port, to the opening of the housing part, and includes a first engagement guide path provided in the distal end member and a second engagement guide path is provided in the treatment tool erection pedestal and connected to the first engagement guide path; and a deformation generating part that is provided at an end part within the first engagement guide path on the second engagement guide path side and, in a case where a direction that extends perpendicularly from an opening surface of the opening toward an outside of the opening is defined as a first direction, comes into contact the engaging part, which advances toward the second engagement guide path inside the first engagement guide path, to displace the engaging part in the first direction, thereby elastically deforming the wire, the second engagement guide path comes into contact with the engaging part, which advances toward the opening, and maintains the elastic deformation of the wire, and the engaging part is housed in the housing part from the opening by a restoring force of the wire in a case where the engaging part has reached the opening.

According to the one aspect, the engaging part delivered from the delivery port advances along the first engagement guide path of the distal end member. Then, in a case where the engaging part comes into contact with the deformation generating part within the first engagement guide path, the engaging part is displaced in the first direction, and the wire is elastically deformed. The engaging part that has passed through the first engagement guide path advances along the second engagement guide path. In this case, the elastic deformation of the wire is maintained. Then, in a case where the engaging part has reached the opening, the engaging part is housed in the housing part from the opening by the restoring force of the wire. That is, according to the one aspect of the invention, the engaging part can be housed in the housing part by utilizing the biasing force that is the restoring force of the wire.

In one aspect of the engaging part is a spherical body, and the housing part is a spherical recess that houses the engaging part that is the spherical body.

According to the one aspect of the invention, the sliding resistance between the engaging part and the housing part, which is caused by the push/pull operation of the wire, is reduced.

In one aspect of the invention, it is preferable that the distal end member is provided with a separation guide surface, which guides the wire in a direction in which the engaging part is separated from an inside of the housing part to the outside of the opening in a case where the wire is operated to be further pushed in a state where the engaging part is housed in the housing part and the treatment tool erection pedestal is located in the lodged position.

According to the one aspect of the invention, in a case where the wire is operated to be further pushed in a state where the treatment tool erection pedestal is located at the lodged position, the wire is guided in the direction in which the engaging part is separated from the inside of the housing part to the outside of the opening by the separation guide surface of the distal end member.

In one aspect of the invention, it is preferable that a separation guide surface, which guides the engaging part in a direction in which the engaging part is separated from an inside of the housing part to the outside of the opening in a case where the wire is operated to be further pushed in a state where the engaging part is housed in the housing part and the treatment tool erection pedestal is located in the lodged position, is formed in the housing part.

According to the one aspect of the invention, in a case where the wire is operated to be further pushed in a state where the treatment tool erection pedestal is located at the lodged position, the housing part is guided in the direction in which the engaging part is separated from the inside of the housing part to the outside of the opening by the separation guide surface of the housing part.

In one aspect of the invention, it is preferable that the housing part is disposed at a position that faces the delivery port in a state where the treatment tool erection pedestal is located at the erected position.

According to the one aspect of the invention, by advancing the engaging part straight from the delivery port, the engaging part can be housed in the housing part of the treatment tool erection pedestal located at the erected position.

In one aspect of the invention, it is preferable that the housing part is disposed at a position that faces the delivery port in a state where the treatment tool erection pedestal is located at the lodged position.

According to the one aspect of the invention, by advancing the engaging part straight from the delivery port, the engaging part can be housed in the housing part of the treatment tool erection pedestal located at the lodged position.

In one aspect of the invention, it is preferable that the treatment tool erection pedestal is provided with a coupling part in which the housing part is formed, and the coupling part is coupled to the treatment tool erection pedestal in a rotationally movable manner about a shaft parallel to a rotational movement shaft of the treatment tool erection pedestal.

According to the one aspect of the invention, since the coupling part is rotationally moved as the treatment tool erection pedestal moves from the lodged position to the erected position by the pulling operating of the wire, the wire between the engaging part and the delivery port can be maintained in a linear shape.

In order to achieve the first object of the invention, a wire attaching method for an endoscope related to the invention comprises an insertion step of inserting a wire having an engaging part provided at a distal end part thereof with the engaging part as a head from an introduction port of a proximal operating part of an endoscope, thereby inserting the wire through an insertion part of the endoscope having a proximal end part connected to the proximal operating part; a delivery step of delivering the wire with the engaging part as a head from a delivery port of a distal end member provided at the distal end part of the insertion part; and a housing step of guiding the engaging part of the wire delivered forward from the delivery port, to an opening of a housing part of the treatment tool erection pedestal attached to the distal end member in a rotationally movable manner, by the engagement guide part by a pushing operation of the wire from the introduction port, and housing the engaging part in the housing part.

According to the invention, first, in the insertion step, the wire is inserted through the insertion part by inserting the wire with the engaging part as a head from the introduction port of the proximal operating part. Next, in the delivery step, the wire is delivered with the engaging part as a head from the delivery port of the distal end member of the insertion part. Next, in the housing step, the engaging part of the wire delivered forward from the delivery port is guided to the opening of the housing part of the treatment tool erection pedestal by the engagement guide part by the delivery operation of the wire from the introduction port, and is housed in the housing part. Accordingly, according to the invention, the distal end part of the wire and the treatment tool erection pedestal can be easily coupled to each other.

In the one aspect of the invention, it is preferable that the wire attaching method for an endoscope further comprises an erected position disposing step as a step before the insertion step, and in the erected position disposing step, the housing part is disposed at a position that faces the delivery port by mounting a protecting member, which protects the distal end member, on the distal end member, and holding the treatment tool erection pedestal at the erected position by a holding part provided in the protecting member.

According to the one aspect of the invention, the treatment tool erection pedestal is held at the erected position by the holding part of the protecting member by mounting the protecting member on the distal end member in the erected position disposing step provided as the step before the insertion step.

In order to achieve the second object of the invention, a wire detaching method for an endoscope related to the invention is a wire detaching method for an endoscope including a step of detaching an engaging part of a distal end part of a wire housed in a housing part of a treatment tool erection pedestal from the housing part, and the method comprises locating the treatment tool erection pedestal at a lodged position by a pushing operation of the wire from an introduction port of a proximal operating part of an endoscope, and then, further pushing the wire, to guide a distal end side of the wire in a direction in which the engaging part is separated from an inside of the housing part to an outside of the opening of the housing part by the separation guide surface, thereby detaching the engaging part from the housing part.

According to the invention, in a case where the wire is operated to be further pushed after the treatment tool erection pedestal is located at the lodged position, the wire is guided in the direction in which the engaging part is separated from the inside of the housing part to the outside of the opening by the separation guide surface of the distal end member. Accordingly, the engaging part is easily separated from the inside of the housing part to the outside of the opening by the restoring force of the wire.

In order to achieve the second object of the invention, a wire detaching method for an endoscope related to the invention is a wire detaching method for an endoscope including a step of detaching an engaging part of a distal end part of a wire housed in a housing part of a treatment tool erection pedestal from the housing part, and the method comprises locating the treatment tool erection pedestal at a lodged position by a pushing operation of the wire from an introduction port of a proximal operating part of an endoscope, and then, further pushing the wire, to guide the engaging part in a direction in which the engaging part is separated from an inside of the housing part to an outside of the opening of the housing part by the separation guide surface, thereby detaching the engaging part from the housing part.

According to the invention, in a case where the wire is operated to be further pushed after the treatment tool erection pedestal is located at the lodged position, the engaging part is guided in the direction in which the engaging part is separated from the inside of the housing part to the outside of the opening by the separation guide surface of the housing part. Accordingly, the engaging part is easily separated from the inside of the housing part to the outside of the opening.

According to the invention, the distal end part of the wire and the treatment tool erection pedestal can be easily coupled to each other. Additionally, the distal end part of the wire can be easily detached from the treatment tool erection pedestal.

BRIEF DESCRIPTION OF THE DRAWINGS

FIG. 7 is an enlarged perspective view in which an engaging part is housed in a housing part via an engagement guide part.

FIG. 12 is an enlarged perspective view in which the engaging part is housed in the housing part via the engagement guide part.

FIG. 16 is an explanatory view of the operation in which the engaging part is guided by the engagement guide part.

FIG. 19 is an enlarged perspective view in which the engaging part is housed in the housing part via the engagement guide part.

FIG. 20 is an explanatory view of the operation in which the engaging part is guided by the engagement guide part and is housed in the housing part.

DESCRIPTION OF THE PREFERRED EMBODIMENTS

Hereinafter, preferable embodiments of an endoscope, a wire attaching method for an endoscope, and a wire detaching method for an endoscope related to the invention will be described with reference to the accompanying drawings.

Figure 1:
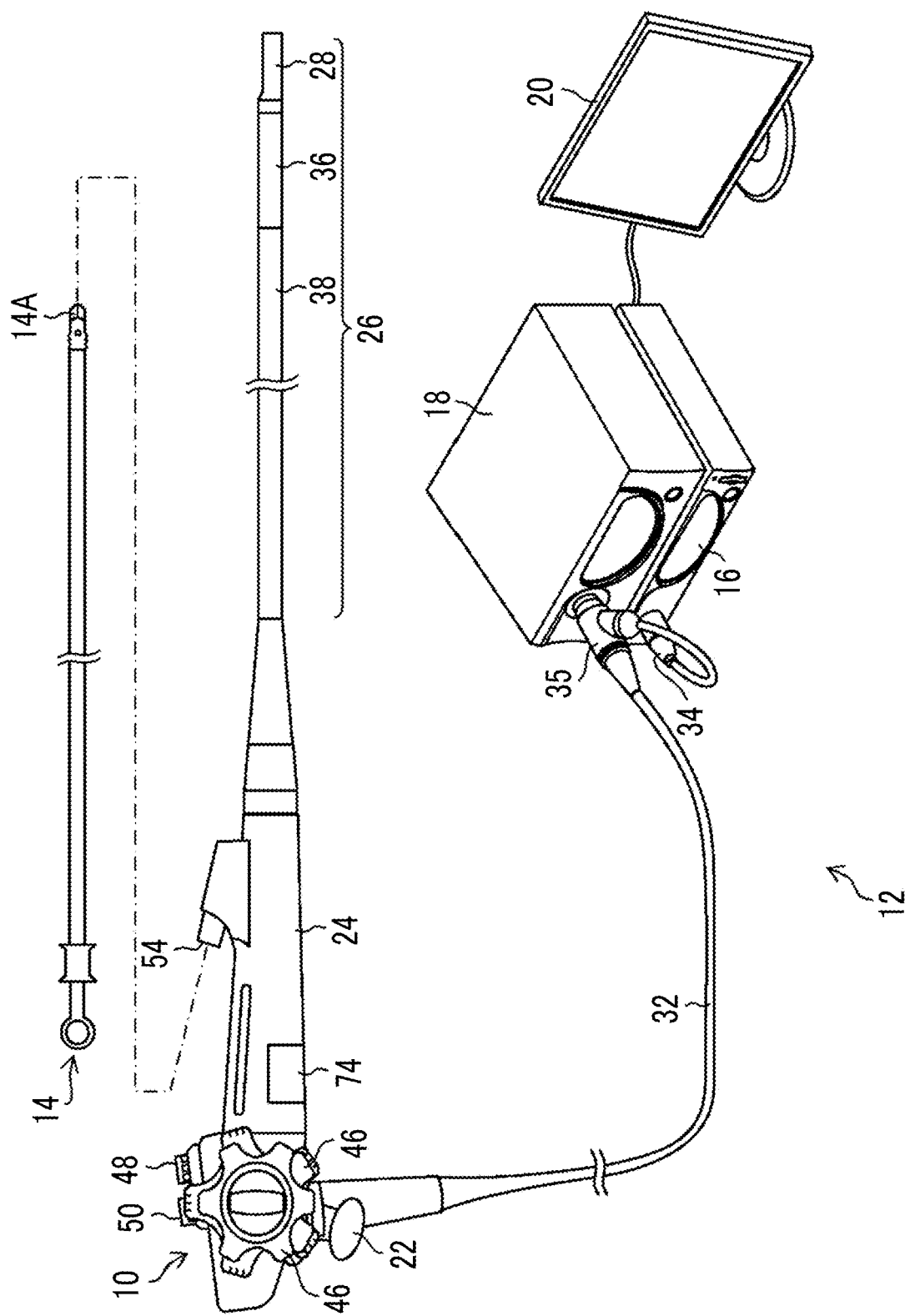
FIG. 1 is a configuration view of an endoscope system comprising an endoscope related to an embodiment.

FIG. 1 is a configuration view of an endoscope system 12 comprising an endoscope 10 related to an embodiment of the invention.

As illustrated in FIG. 1, the endoscope system 12 comprises the endoscope 10, a processor device 16, a light source device 18, and a display 20.

[Configuration of Endoscope 10]

Figure 2:
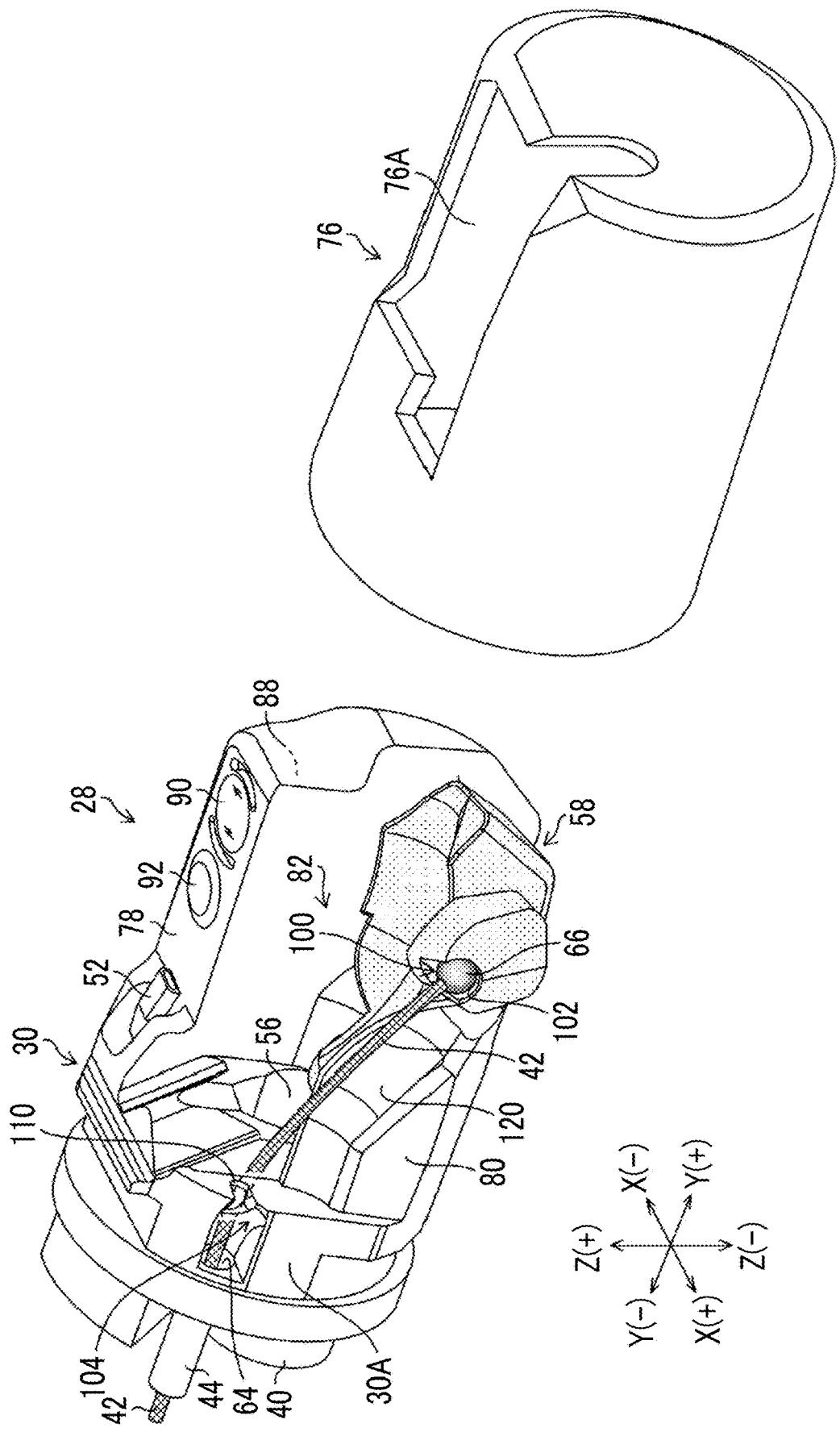
FIG. 2 is a perspective view of a distal end member where an erection pedestal is located at a lodged position.
Figure 3:
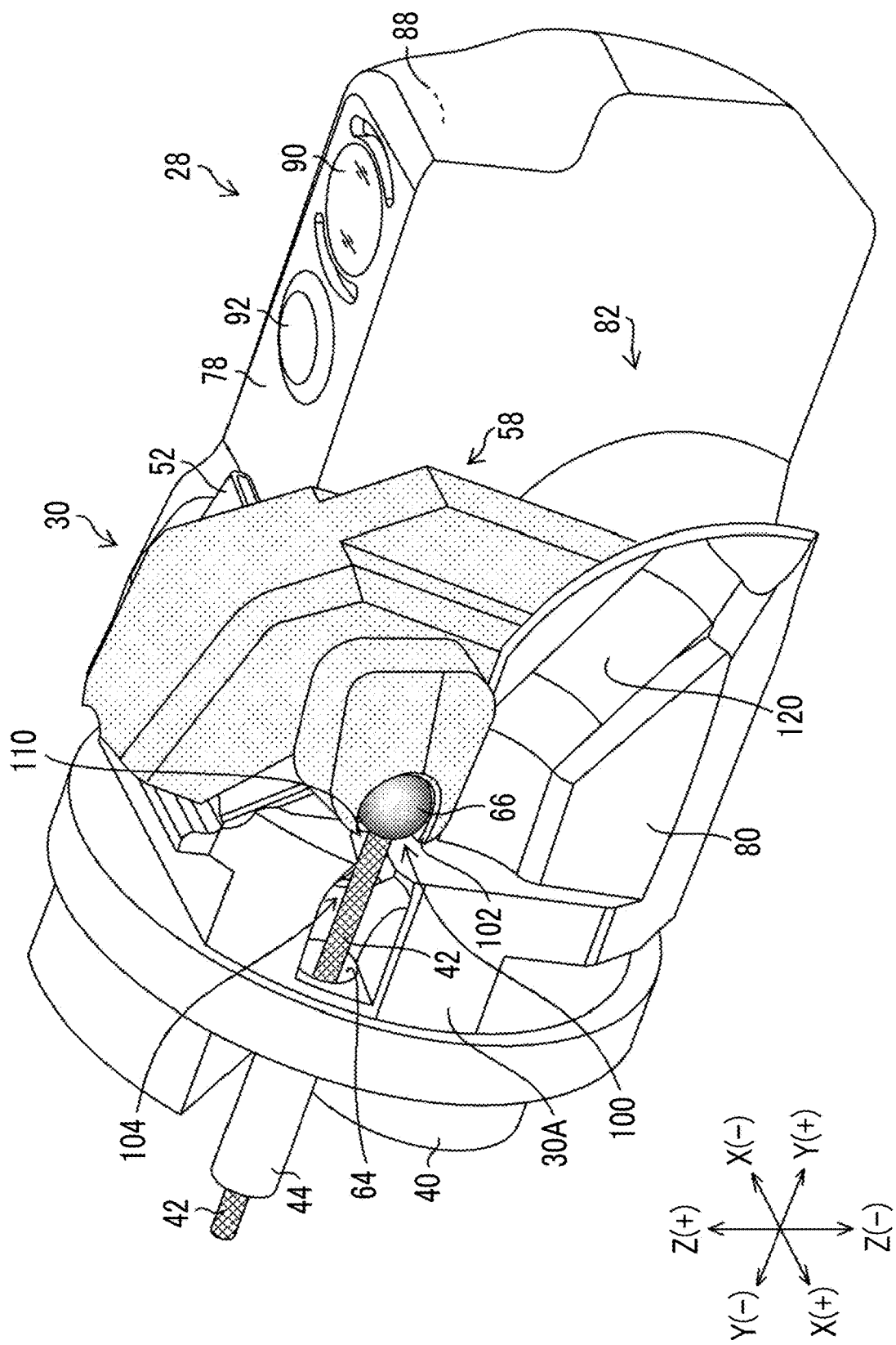
FIG. 3 is a perspective view of the distal end member where the erection pedestal is located at an erected position.

The endoscope 10 comprises an operating part 24 comprising an erection lever 22 that is an operating member, and an insertion part 26 having a proximal end part connected to the operating part 24. Additionally, as illustrated in perspective views of FIGS. 2 and 3 illustrating the configuration of the distal end part 28 of the insertion part 26, the distal end part 28 of the insertion part 26 is provided with a distal end member 30. FIG. 2 is a perspective view of the distal end member 30 in which an erection pedestal 58 to be described below is located at a lodged position, and FIG. 3 is a perspective view of the distal end member 30 in which the erection pedestal 58 is located at an erected position. In addition, in the following description, an upward direction refers to a Z(+) direction of FIG. 2, a downward direction refers to a Z(−) direction of FIG. 2, a rightward direction refers to an X(+) direction of FIG. 2, and a leftward direction refers to an X(−) direction of FIG. 2. Additionally, the Y(+) direction of FIG. 2 refers to a distal-end-side direction of the distal end member 30, and the Y(−) direction of FIG. 2 refers to a proximal-end-side direction of the distal end member 30.

Referring back to FIG. 1, the operating part 24 is provided with a universal cord 32 to be connected to the processor device 16 and the light source device 18. A pair of connectors 34 and 35 is branched and attached to a distal end side of the universal cord 32, the connector 34 is connected to the processor device 16, and the connector 35 is connected to the light source device 18.

The insertion part 26 is configured such that the distal end part 28, a bending part 36, and a flexible part 38 are coupled to each other from a distal end side toward a proximal end side.

Built-in elements, such as a treatment tool insertion channel 40 (refer to FIG. 2) that guides a distal end part of a treatment tool 14 to the distal end member 30 (refer to FIG. 2), a wire 42 (refer to FIG. 2) for performing the operation of changing a delivery direction of the distal end part of the treatment tool 14 to be delivered from the distal end member 30, a light guide (not illustrated) that guides illumination light to be supplied from the light source device 18 to the distal end member 30, an air and water supply tube (not illustrated), angle wires (not illustrated), and a signal cable (not illustrated), are inserted through the inside of the insertion part 26. Additionally, the wire 42 is inserted through a wire insertion channel 44 (refer to FIG. 2) inserted through the insertion part 26 and is protected.

A pair of angle knobs 46 and 46 that performs the bending operation of the bending part 36 is coaxially provided in a rotationally movable manner on a side surface of the operating part 24 of FIG. 1. The bending part 36 has a structural body in which a plurality of angle ring (not illustrated) is coupled to each other in a rotationally movable manner. The bending part 36 is configured by covering an outer periphery of the structural body with a tubular net knit with metal wires and covering an outer peripheral surface of the net with a tubular outer cover made of rubber. For example, four angle wires (not illustrated) are disposed from the bending part 36 configured in this way to the angle knobs 46 and 46, and the bending part 36 is vertically and horizontally bent by performing the push/pull operation of the angle wires by the rotational movement operation of the angle knobs 46 and 46.

Additionally, an air/water supply button 48 and a suction button 50 are provided side by side on an upper surface of the operating part 24. By operating the air/water supply button 48, air and water can be sprayed from an air/water supply nozzle 52 (refer to FIG. 2) provided in the distal end member 30. Additionally, by operating the suction button 50, body fluids, such as blood, can be suctioned from a suction port that also serves as a treatment tool delivery port 56 provided in the distal end member 30.

Moreover, a treatment tool introduction port 54 for introducing the treatment tool 14 is provided on a distal end side of the operating part 24. The treatment tool 14 introduced with a distal end part as a head from the treatment tool introduction port 54 is delivered from the treatment tool delivery port 56 (refer to FIG. 2) provided in the distal end member 30 via the treatment tool insertion channel 40 (refer to FIG. 2) inserted through the insertion part 26 to the outside.

Furthermore, the erection lever 22 is provided in a rotationally movable manner on the side surface of the operating part 24. The rotational movement operation of the erection lever 22 is performed by a surgeon that grips the operating part 24. In a case where the rotational movement operation of the erection lever 22 is performed, the wire 42 (refer to FIG. 2) coupled to the erection lever 22 on a proximal end side thereof is pushed and pulled, and the posture of the erection pedestal 58 coupled to a distal end side of the wire 42 is changed between the erected position of FIG. 3 and the lodged position of FIG. 2.

Figure 4:
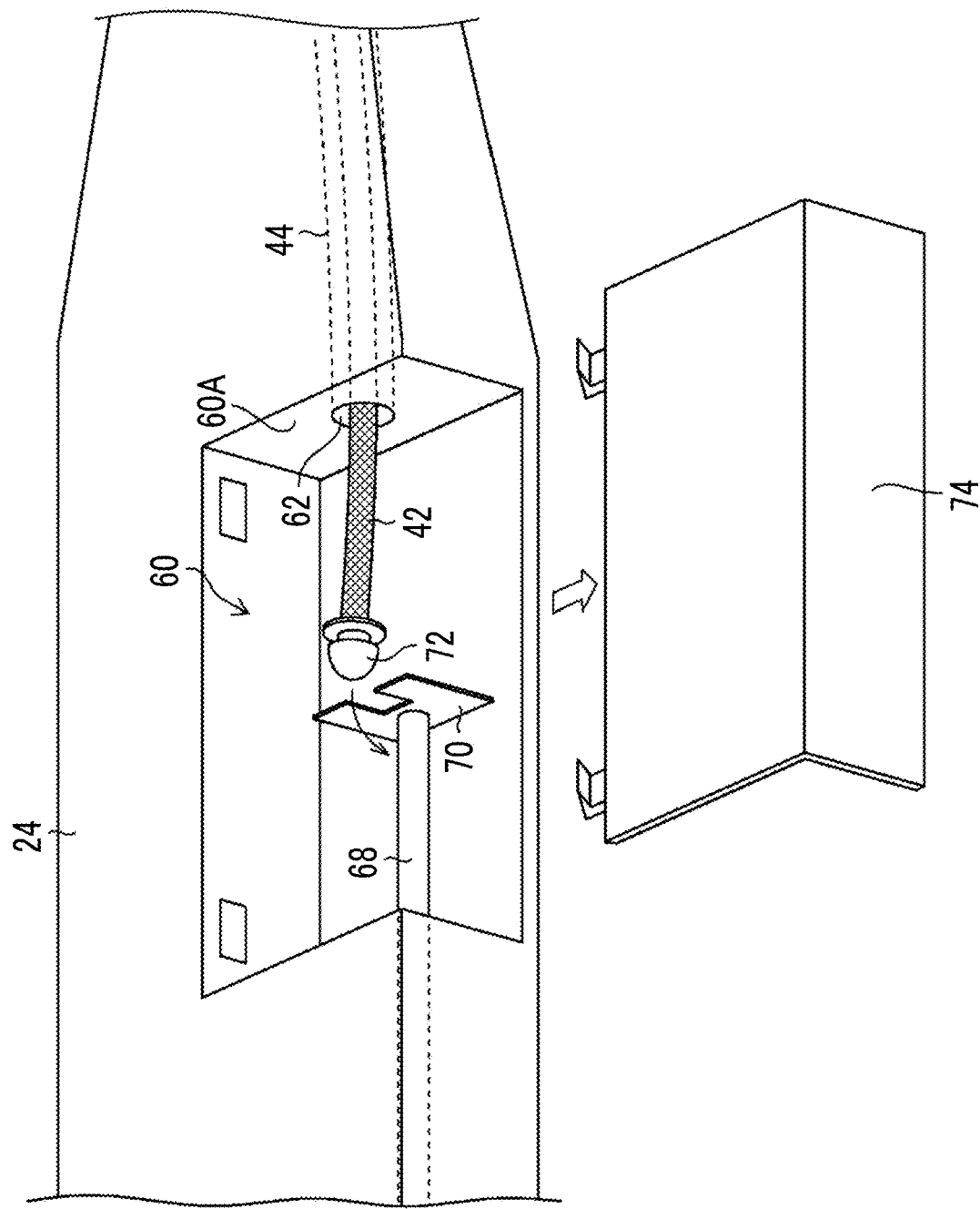
FIG. 4 is an enlarged view illustrating the configuration of main parts of an operating part.

FIG. 4 is an enlarged view illustrating the configuration of main parts of the operating part 24.

As illustrated in FIG. 4, the operating part 24 is provided with a recess 60 in which the proximal end part of the wire 42 is disposed. An introduction port 62 into which the wire 42 is introduced is formed in a wall surface 60A on a distal end side of the recess 60. A proximal end part of the wire insertion channel 44 of FIG. 2 is connected to this introduction port 62, and a distal end part of the wire insertion channel 44 is connected to a delivery port 64 provided in the distal end member 30. That is, the wire insertion channel 44, which communicates the introduction port 62 provided in the operating part 24 with the delivery port 64 provided in the distal end member 30, is provided inside the insertion part 26. Additionally, a distal end part of the wire 42 is provided with an engaging part 66 (refer to FIG. 2) to be described below, and the wire 42 is introduced from the introduction port 62 with the engaging part 66 as a head, and is delivered from the delivery port 64 with the engaging part 66 as a head.

Additionally, a distal end engaging part 70 of a drive shaft 68 is disposed in the recess 60 of FIG. 4. The drive shaft 68 is reciprocally moved by the rotational movement operation of the erection lever 22 (refer to FIG. 1) in an insertion direction of the wire 42, and a proximal end engaging part 72 of the wire 42 is attachably and detachably engaged with the distal end engaging part 70 of a distal end of the drive shaft 68. Accordingly, the erection lever 22 and the wire 42 are coupled to each other via the drive shaft 68. The recess 60 is closed by a cover 74 that is attachable to and detachable from the recess 60.

In addition, the flexible part 38 illustrated in FIG. 1 has a spiral tube (not illustrated) formed by spirally winding a thin metallic beltlike sheet having elasticity. The flexible part 38 is configured by covering the outside of the spiral tube with a tubular net knit with metal wires and covering an outer peripheral surface of the net with a tubular outer cover made of resin.

The endoscope 10 of the embodiment configured as described above is a side viewing endoscope used as a duodenum mirror, and treatment, such as predetermined examination or remedy, is performed by the insertion part 26 being inserted into the body via the mouth and the insertion part 26 being inserted from the esophagus through the stomach into the duodenum.

In the embodiment, biopsy forceps having a cup 14A capable of extracting living body tissue at a distal end part thereof are exemplified as the treatment tool 14. However, treatment tools, such as an imaging tube or a knife for endoscopic sphincterotomy (EST) are used as other treatment tools.

[Configuration of Distal End Part 28]

As illustrated in FIG. 2, the distal end part 28 of the insertion part 26 is constituted of the distal end member 30, and a cap 76 attachably and detachably mounted on the distal end member 30. The cap 76 is formed in a substantially tubular shape that is sealed on a distal end side thereof, and a substantially rectangular opening window 76A is formed in a portion of an outer peripheral surface of the cap 76. In a case where the cap 76 is mounted on the distal end member 30, the treatment tool delivery port 56 and the opening window 76A are allowed to communicate with each other. Accordingly, the distal end part of the treatment tool 14 delivered from the treatment tool delivery port 56 is delivered from the opening window 76A to the outside.

The cap 76 is made of materials with an elastic force, for example, rubber materials, such as fluororubber and silicone rubber, or resin materials, such as polysulfone, has an engaging part (not illustrated) to be engaged with a groove (not illustrated) formed in the distal end member 30, on a proximal end side thereof, and is mounted on the distal end member 30 by engaging the engaging part with the groove of the distal end member 30. Additionally, in a case where the treatment of the endoscope 10 is completed, the cap 76 is detached from the distal end member 30 and cleaned and disinfected, or is discarded as disposable.

[Configuration of Distal End Member 30]

As illustrated in FIGS. 2 and 3, the distal end member 30 is made of metallic materials having corrosion resistance. Additionally, a partition wall 78 provided to protrude toward the distal end side and a partition wall 80 that faces the partition wall 78 are integrally provided in the distal end member 30. An erection pedestal housing chamber 82 that houses the erection pedestal 58 is formed between the partition wall 78 and the partition wall 80. The treatment tool delivery port 56 for delivering the treatment tool 14 to the outside is formed on a proximal end side of the erection pedestal housing chamber 82, and a distal end part of the treatment tool insertion channel 40 is connected to the treatment tool delivery port 56. In addition, the treatment tool insertion channel 40 is inserted through the inside of the insertion part 26 of FIG. 1, and a proximal end part of the treatment tool insertion channel 40 is connected to the treatment tool introduction port 54 of the operating part 24. Therefore, the distal end part of the treatment tool 14 introduced into the treatment tool insertion channel 40 from the treatment tool introduction port 54 is delivered from the treatment tool delivery port 56 to the erection pedestal housing chamber 82 via the treatment tool insertion channel 40. The delivery direction of the distal end part of the treatment tool 14 delivered to the erection pedestal housing chamber 82 is changed depending on the posture between the erected position and the lodged position of the erection pedestal 58 disposed in the erection pedestal housing chamber 82.

<Configuration of Erection Pedestal 58>

As illustrated in FIGS. 2 and 3, the erection pedestal 58 is attached to the distal end member 30 in a rotationally movable manner between the erected position and the lodged position.

Figure 5:
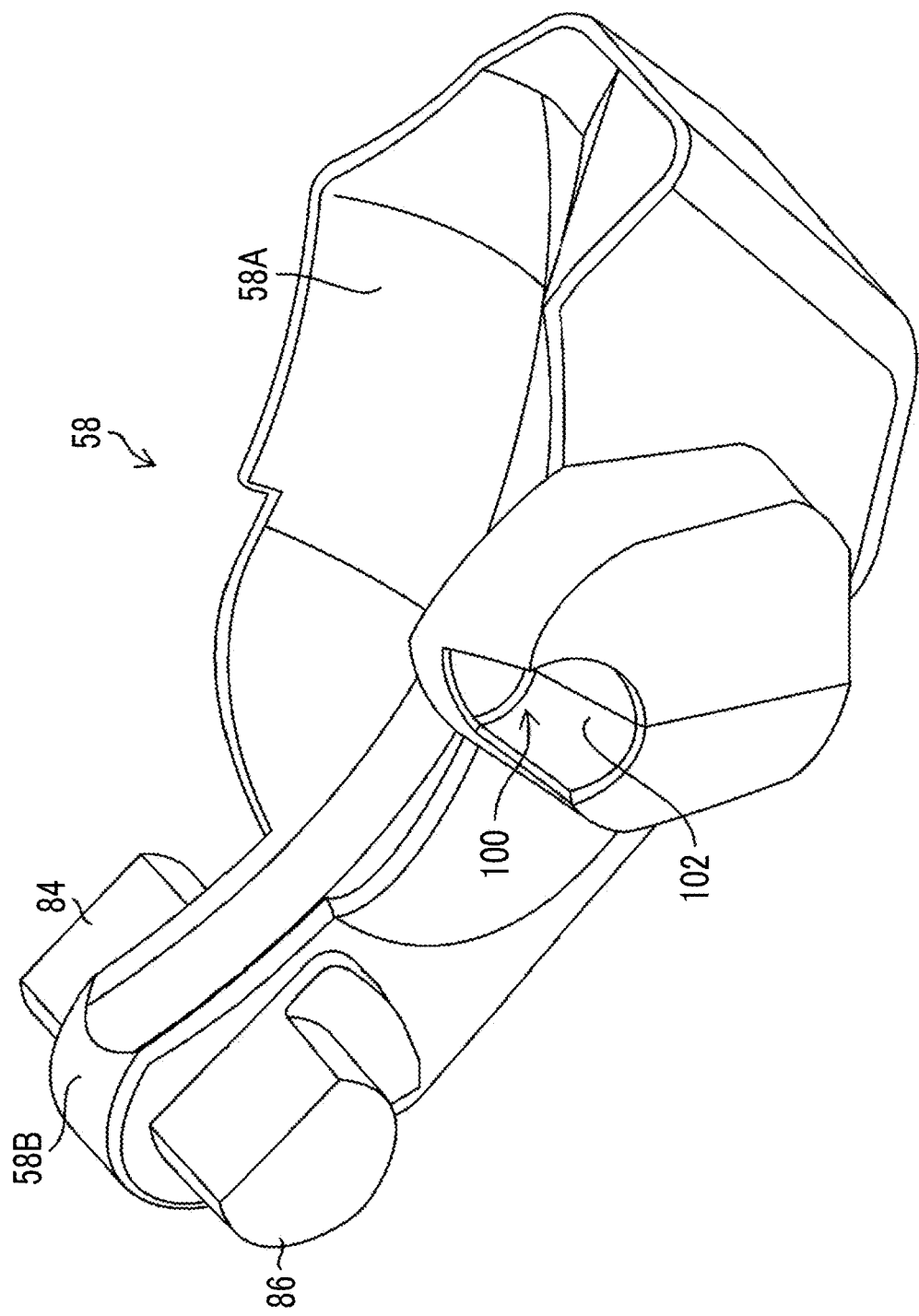
FIG. 5 is an enlarged perspective view of the erection pedestal.

FIG. 5 is an enlarged perspective view of the erection pedestal 58. As illustrated in FIG. 5, an upper surface of the erection pedestal 58 is provided with a guide surface 58A. The distal end part of the treatment tool 14 is delivered from the opening window 76A (refer to FIG. 2) of the cap 76 to the outside along the guide surface 58A.

Both side surfaces of a base part 58B of the erection pedestal 58 are provided with rotational movement shafts 84 and 86. An axial direction of the rotational movement shafts 84 and 86 is set as an X(+)-X(−) direction that is the leftward-rightward direction of FIG. 2 in a case where the erection pedestal 58 is attached to the distal end member 30. In addition, the X(+)-X(−) direction is a direction orthogonal to a Y(+)-Y(−) direction that is the same direction as the axial direction of the distal end member 30 and orthogonal to the Z(+)-Z(−) direction that is the upward-downward direction.

Figure 6:
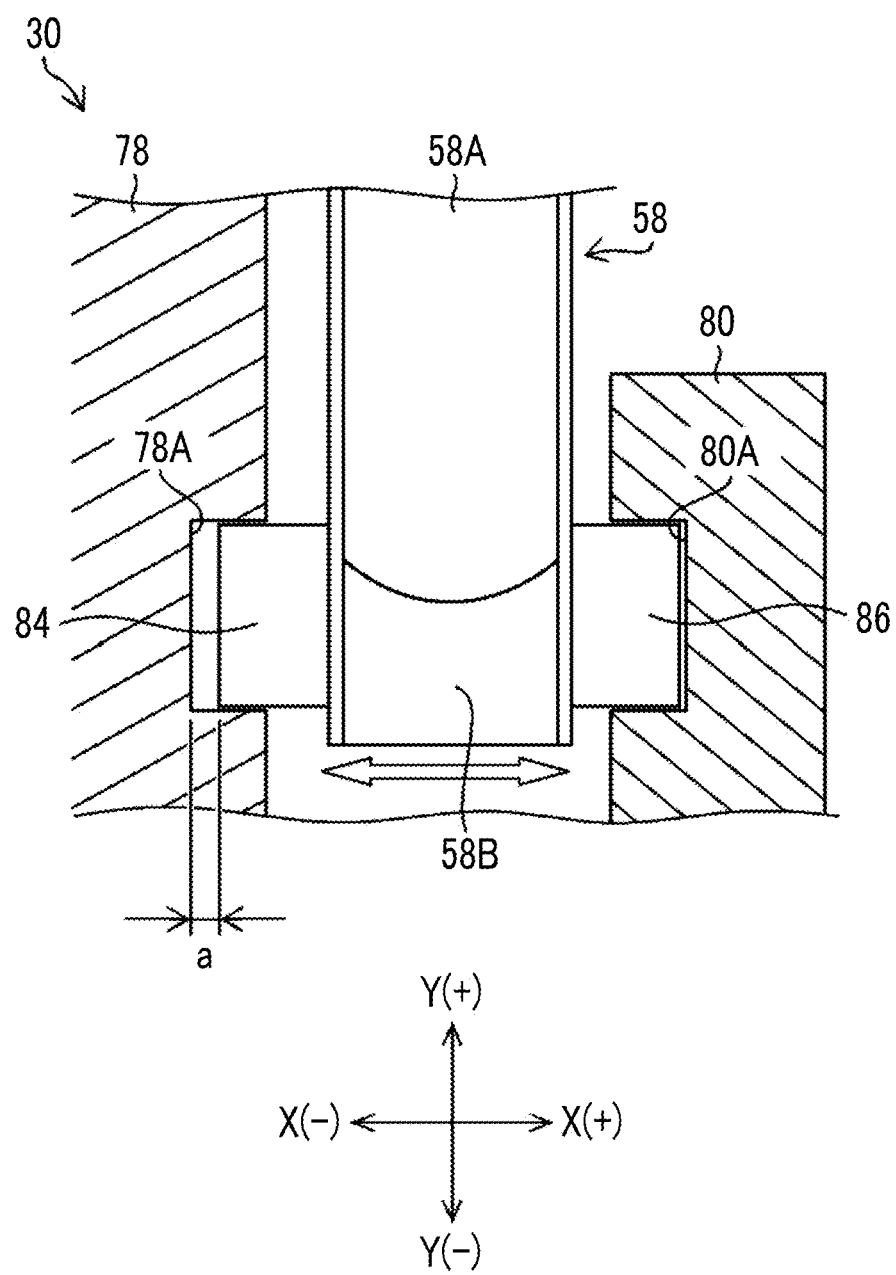
FIG. 6 is a cross-sectional view of main parts view illustrating an attachment structure of the erection pedestal with respect to the distal end member.

FIG. 6 is a cross-sectional view of main parts illustrating an attachment structure of the erection pedestal 58 with respect to the distal end member 30. As illustrated in FIG. 6, the rotational movement shafts 84 and 86 are coaxially disposed via the base part 58B of the erection pedestal 58, the rotational movement shaft 84 is fitted to a concave bearing part 78A of the partition wall 78 in a rotationally movable manner, and the rotational movement shaft 86 is fitted to a concave bearing part 80A of the partition wall 80 in a rotationally movable manner. Additionally, the rotational movement shafts 84 and 86 is mounted on to the bearing parts 78A and 80A, respectively, with a predetermined rattling amount a in the axial direction of the rotational movement shafts 84 and 86. In a case where the rotational movement shafts 84 and 86 are biased to one side by utilizing the rattling amount a, a portion of one bearing part of the bearing parts 78A and 80A can be exposed and a brush can be easily inserted into the exposed portion. Thus, the cleaning performance of the bearing parts 78A and 80A is improved.

<Other Configurations of Distal End Member 30>

As illustrated in FIGS. 2 and 3, an optical system housing chamber 88 is provided inside the partition wall 78. An illumination window 90 and an observation window 92 are disposed adjacent to each other at an upper part of the optical system housing chamber 88, and the air/water supply nozzle 52 directed to the observation window 92 is provided in the distal end member 30. The air/water supply nozzle 52 is connected to an air/water supply device (not illustrated) via the air and water supply tube (not illustrated) inserted through the insertion part 26, and air or water is sprayed from the air/water supply nozzle 52 toward the observation window 92 by operating the air/water supply button 48 of the operating part 24 illustrated in FIG. 1. Accordingly, the observation window 92 is cleaned.

Additionally, an illumination unit (not illustrated) and an imaging unit (not illustrated) are housed inside the optical system housing chamber 88. The illumination unit comprises an illumination lens (not illustrated) installed inside the illumination window 90, and the light guide (not illustrated) disposed such that a distal end surface thereof faces the illumination lens. The light guide is disposed in the universal cord 32 via the operating part 24 from the insertion part 26 of the endoscope 10, and has a proximal end connected to the light source device 18 via the connector 35. Accordingly, the radiated light from the light source device 18 is transmitted via the light guide and is radiated from the illumination window 90 to the outside.

The imaging unit comprises an imaging optical system (not illustrated) inside the observation window 92, and a complementary metal oxide semiconductor (CMOS) type or charge coupled device (CCD) type image pickup element. The image pickup element is connected to the processor device 16 via the signal cable (not illustrated) inserted through the insertion part 26 of FIG. 1. After image pickup signals of a subject image obtained by the imaging unit is output to the processor device 16 via the signal cable and subjected to image processing, the image pickup signals are displayed as the subject image on the display 20.

[Coupling Structure of Wire 42 and Erection Pedestal 58]

Next, a coupling structure in which the distal end part of the wire 42 is coupled to the erection pedestal 58 will be described.

Although being overlapped with the earlier description, first, describing the wire 42, as illustrated in FIGS. 2 and 3, the wire 42 rotationally moves the erection pedestal 58 by being coupled to the erection pedestal 58 on the distal end side thereof, being coupled to the erection lever 22 of FIG. 1 on the proximal end side thereof, being pushed and pulled depending on the operation of the erection lever 22. The distal end part of this wire 42 is provided with the engaging part 66. The erection pedestal 58 is provided with a housing part 100 that houses the engaging part 66 and that has an opening 102 formed on an X(+) direction side and has a bottom surface formed on an X(−) direction side. That is, the distal end part of the wire 42 is coupled to the erection pedestal 58 by housing the engaging part 66 provided in the distal end part of the wire 42 in the housing part 100 via the opening 102.

In the embodiment, the engaging part 66 is a spherical body, and the housing part 100 is a spherical recess that houses the engaging part 66 of the spherical body. In addition, although the shapes of the engaging part 66 and the housing part 100 are not limited to the above shapes, the sliding resistance between the engaging part 66 and the housing part 100, which is caused by the push/pull operation of the wire 42, can be reduced by forming the engaging part 66 as the spherical body and forming the housing part 100 as the spherical recess. Thus, the push/pull operation of the wire 42 can be smoothly performed.

Additionally, the coupling structure between the wire 42 and the erection pedestal 58 is provided with an engagement guide part 104 of a first form that is installed consecutively with the housing part 100 at the erected position of FIG. 3. The engagement guide part 104 of the first form is provided in the distal end member 30, and has a function of guiding the engaging part 66 delivered from the delivery port 64, to the opening 102 of the housing part 100.

According to the endoscope 10 having the engagement guide part 104 of the first form, in a case where the wire 42 is introduced with the engaging part 66 as a head from the introduction port 62 (refer to FIG. 4) of the operating part 24, the engaging part 66 passes through the wire insertion channel 44 and is delivered from the delivery port 64 (refer to FIG. 2) of the distal end member 30 to the outside. Then, the engaging part 66 is guided toward the opening 102 of the housing part 100 of the erection pedestal 58 by the engagement guide part 104 by the continued introduction operation of the wire 42, and is housed in the housing part 100 from the opening 102. Accordingly, according to the endoscope 10 of the embodiment, since the engaging part 66 of the wire 42 can be housed in the housing part 100 of the erection pedestal 58 simply by the introduction operation of the wire 42, the distal end part of the wire 42 and erection pedestal 58 can be easily coupled to each other.

<Configuration of Engagement Guide Part 104 of First Form>

Next, the configuration of the engagement guide part 104 of the first form will be described.

Figure 8:
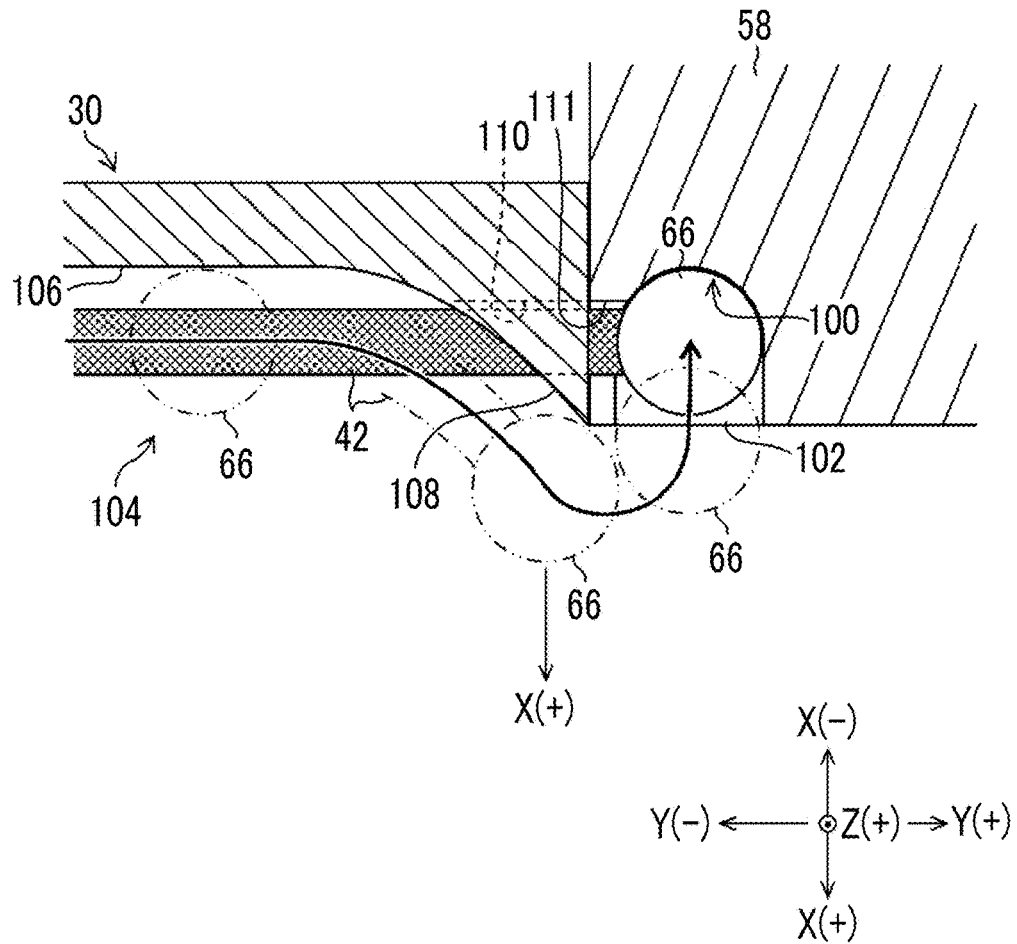
FIG. 8 is an explanatory view of the operation in which the engaging part is guided by the engagement guide part and is housed in the housing part.

FIG. 7 is an enlarged perspective view in which the engaging part 66 is housed in the housing part 100 via the engagement guide part 104. FIG. 8 is an explanatory view sequentially illustrating the operation until the engaging part 66 is guided by the engagement guide part 104 and housed in the housing part 100.

As illustrated in FIGS. 7 and 8, the engagement guide part 104 comprises an engagement guide path 106 that guides the engaging part 66 delivered from the delivery port 64, to the opening 102 of the housing part 100 in a direction from the delivery port 64 toward the housing part 100. Additionally, the engagement guide part 104 comprises a deformation generating part 108 installed consecutively with the opening 102 of the housing part 100, within the engagement guide path 106. The deformation generating part 108 comes into contact with the engaging part 66 that advances in the Y(+) direction toward the opening 102 within the engagement guide path 106, guides the engaging part 66 in the Y(+) direction, and guides the engaging part 66 in the X(+) direction. Accordingly, on the distal end side of the wire 42, the engaging part 66 is elastically deformed in a direction (the X(+) direction) from the bottom surface of the housing part 100 toward the opening 102 as the engaging part 66 approaches the opening 102 along the engagement guide path 106. In a case where the engaging part 66 that advances within the engagement guide path 106 has passed by the deformation generating part 108, the engaging part 66 is moved in the X(−) direction by a restoring force of the wire 42, and is housed in the housing part 100 from the opening 102. Here, the direction from the bottom surface of the housing part 100 toward the opening 102 means a direction from the center of the bottom surface of the housing part 100 toward the center of the opening 102. However, the invention is not limited to this, and the direction from the bottom surface of the housing part 100 toward the opening 102 is a direction including at least a component in a direction opposite to a direction that is oriented in a case where the engaging part 66 is housed in the housing part 100.

The engagement guide path 106 of the engagement guide part 104 is formed by concavely cutting away a portion of a peripheral surface 30A of the distal end member 30, and is a surface that is gradually inclined in the X(+) direction from the delivery port 64 toward the Y(+) direction. The deformation generating part 108 is formed on a distal end side of the engagement guide path 106.

Additionally, a groove 110 for allowing the distal end side of the wire 42 to sink and escape in a case where the engaging part 66 is housed in the housing part 100, is formed in the engagement guide part 104. Additionally, a groove 111 for allowing the distal end side of the wire 42 to sink and escape in a case where the engaging part 66 is housed in the housing part 100 is also formed on a proximal end side of the housing part 100 of the erection pedestal 58. The width dimension of the groove 110 in a direction orthogonal to the paper plane of FIG. 8 is larger than the diameter of the wire 42, and is smaller than the diameter of the engaging part 66 such that the engaging part 66 passing through the deformation generating part 108 does not sink in the groove 110. Additionally, the width dimension of the groove 111 of in a direction orthogonal to the paper plane of FIG. 8 is larger than the diameter of the wire 42, and is smaller than the diameter of the engaging part 66 such that the engaging part 66 housed in the housing part 100 does not slip off in the Y(−) direction.

The engagement guide part 104 of the first form has a form in which the engagement guide part 104 is provided in the distal end member 30 and a form that is suitable in a case where the engaging part 66 is housed in the housing part 100 in a state where the erection pedestal 58 is located at the erected position. That is, as illustrated in FIG. 7, the housing part 100 is disposed at a position that faces the delivery port 64 in a state where the erection pedestal 58 is located at the erected position. Therefore, by advancing the engaging part 66 straight from the delivery port 64, the engaging part 66 can be housed in the housing part 100 of the erection pedestal 58 located at the erected position via the engagement guide part 104.

According to the endoscope 10 having the engagement guide part 104 of the first form, the engaging part 66 delivered from the delivery port 64 advances while being guided to the opening 102 of the housing part 100 by the engagement guide path 106. In this case, in a case where the engaging part 66 comes into contact with the deformation generating part 108, the engaging part 66 is guided in the direction from the bottom surface of the housing part 100 toward the opening 102, that is, in the X(+) direction. Accordingly, the distal end side of the wire 42 is elastically deformed in the direction (the X(+) direction) from the bottom surface of the housing part 100 toward the opening 102. Then, in a case where the engaging part 66 that advances within the engagement guide path 106 has passed by the deformation generating part 108, the engaging part 66 is moved in the X(−) direction by the restoring force of the wire 42, and is housed in the housing part 100 from the opening 102. That is, by providing the engagement guide part 104 with the deformation generating part 108, the engaging part 66 can be housed in the housing part 100 by utilizing a biasing force that is the restoring force of the wire 42.

[Wire Attaching Method]

Next, an example of a wire attaching method of the endoscope 10 related to the embodiment will be described.

Figure 9:
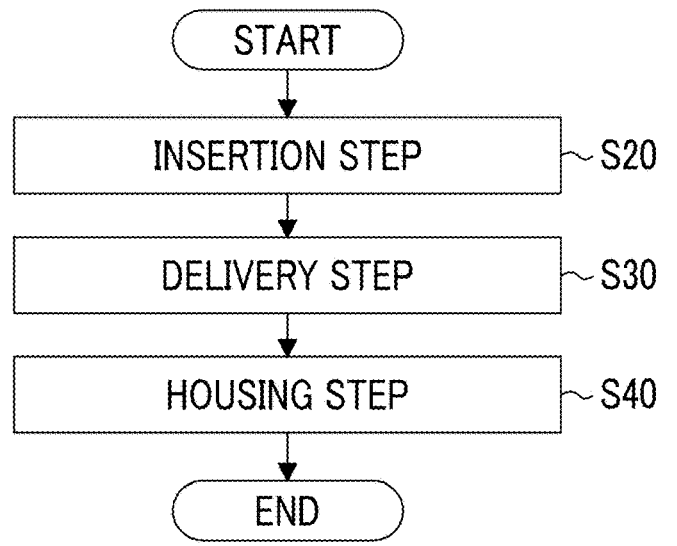
FIG. 9 is a flowchart illustrating the wire attaching method.

FIG. 9 is a flowchart illustrating the wire attaching method of the embodiment.

The wire attaching method of the embodiment comprises an insertion step (S(Step)20), a delivery step (S30), and a housing step (S40).

The insertion step (S20) is a step of inserting the wire 42 having the engaging part 66 provided at the distal end part thereof with the engaging part 66 as a head from the introduction port 62 (refer to FIG. 4) of the operating part 24, thereby inserting the wire 42 through the insertion part 26. Additionally, the delivery step (S30) is a step of delivering the wire 42 with the engaging part 66 as a head from the delivery port 64 of the distal end member 30. Additionally, the housing step (S40) is a step of guiding the engaging part 66 of the wire 42 delivered forward from the delivery port 64, toward the opening 102 of the housing part 100 of the erection pedestal 58 by the engagement guide part 104, by the pushing operation of the wire 42 from an introduction port 62, and housing the engaging part 66 in the housing part 100.

According to the wire attaching method of the embodiment, first, an operator manually holds the erection pedestal 58 at then erected position. Thereafter, in the insertion step (S20), the wire 42 is inserted through the insertion part 26 by inserting the wire 42 with the engaging part 66 as a head from the introduction port 62 of the operating part 24. Next, in the delivery step (S30), the wire 42 is delivered with the engaging part 66 as a head from the delivery port 64 of the distal end member 30. Next, in the housing step (S40), in a case where delivery operation of the wire 42 continues being performed, the engaging part 66 delivered from the delivery port 64 advances while being guided to the opening 102 of the housing part 100 by the engagement guide path 106. In this case, in a case where the engaging part 66 comes into contact with the deformation generating part 108, the engaging part 66 is guided in the direction from the bottom surface of the housing part 100 toward the opening 102, that is, in the X(+) direction. Accordingly, the distal end side of the wire 42 is elastically deformed in the direction (the X(+) direction) from the bottom surface of the housing part 100 toward the opening 102. Then, in a case where the engaging part 66 that advances within the engagement guide path 106 has passed by the deformation generating part 108, the engaging part 66 is moved in the X(−) direction by the restoring force of the wire 42, and is housed in the housing part 100 from the opening 102. Accordingly, according to the wire attaching method of the embodiment, since the wire 42 and the erection pedestal 58 can be coupled to each other simply by the delivery operation of the wire 42, the distal end part of the wire 42 and the erection pedestal 58 can be easily coupled to each other.

Thereafter, as illustrated in FIG. 4, the proximal end engaging part 72 of the wire 42 is engaged with the distal end engaging part 70 of the drive shaft 68, the wire 42 is coupled to the erection lever 22, and the cover 74 is mounted on the operating part 24. The coupling operation between the distal end part of the wire 42 and the erection pedestal 58 is completed above.

Figure 10:
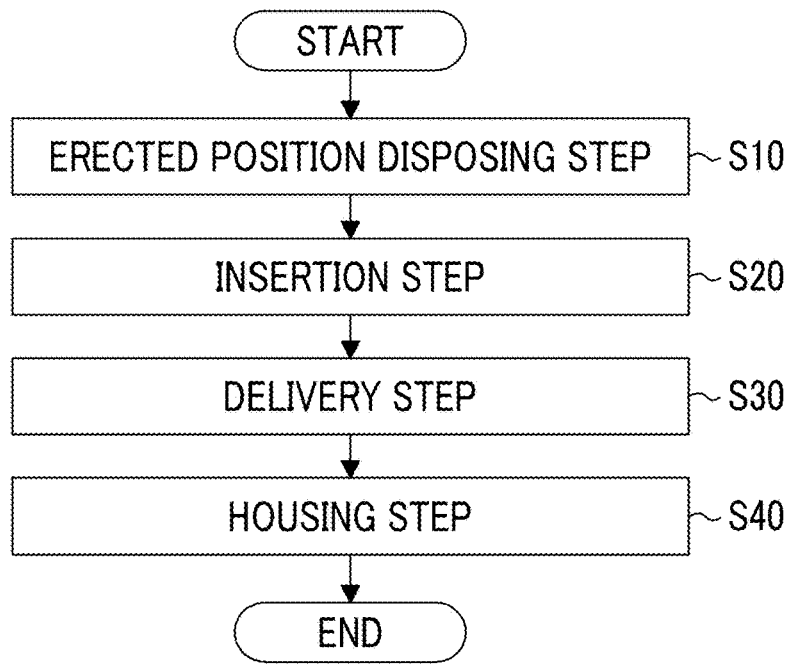
FIG. 10 is a flowchart illustrating another wire attaching method.

Another wire attaching method of the embodiment is illustrated in a flowchart of FIG. 10. The embodiment illustrated in FIG. 10 comprises an erected position disposing step (S10) utilizing a protecting member 112 (refer to FIG. 11) as a step before the insertion step (S20) illustrated in FIG. 9.

Figure 11:
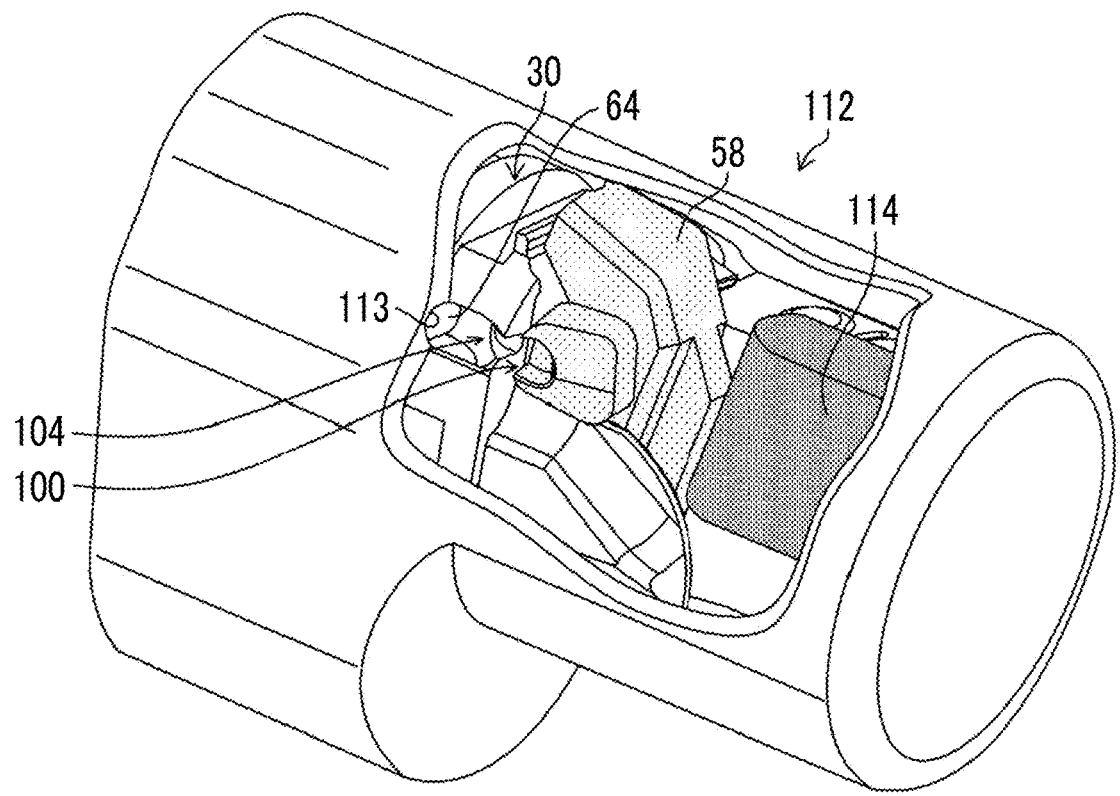
FIG. 11 is an appearance view of a protecting member to be mounted to the distal end member.

An appearance view of the protecting member 112, which is used in the erected position disposing step (S10) and is mounted on the distal end member 30, is illustrated in FIG. 11. Additionally, in order to illustrate the inside of the protecting member 112, the protecting member 112 is partially cut away and illustrated in FIG. 11. The protecting member 112 is mounted on the distal end member 30 at the time of storage of an endoscope 10 to protect the distal end member 30, and is detached from the distal end member 30 at the time of use of the endoscope 10. The protecting member 112 is formed in a substantially tubular shape that is sealed on a distal end side thereof, and a holding part 114, which comes into contact with the erection pedestal 58 and holds the erection pedestal 58 at the erected position, is provided inside the protecting member 112.

In the erected position disposing step (S10), the housing part 100 is disposed at the position that faces the delivery port 64 by mounting the protecting member 112 on the distal end member 30 and holding the erection pedestal 58 at the erected position by the holding part 114 of the protecting member 112. Thereafter, the insertion step (S20), the delivery step (S30), and the housing step (S40), which are described in FIG. 9, are sequentially executed, and the engaging part 66, and the erection pedestal 58 are coupled to each other. Thereafter, the protecting member 112 is detached from the distal end member 30 at the time of the use of the endoscope 10, and the cap 76 illustrated in FIG. 2 is mounted on the distal end member 30.

According to the embodiment comprising the erected position disposing step (S10) utilizing the protecting member 112, the erection pedestal 58 can be easily held at the erected position that is a coupling position between the engaging part 66 and the housing part 100 by mounting the protecting member 112 on the distal end member 30. That is, although it is extremely troublesome for the operator manually holds the small-sized erection pedestal 58 at the erected position, the erection pedestal 58 can be easily held at the erected position simply by mounting the protecting member 112 on the distal end member 30. Accordingly, the coupling operation between the engaging part 66 and the erection pedestal 58 can be easily performed.

In the above embodiment, the engaging part 66 is guided by the engagement guide part 104 in a state where the erection pedestal 58 is held by the protecting member 112 at the erected position. However, a groove 113 that guides the engaging part 66 delivered from the delivery port 64, toward the opening 102, may be formed in a portion of an inner peripheral surface of the protecting member 112 and in a portion that faces the engagement guide part 104. According to this aspect, in a case where the engaging part 66 is guided by the engagement guide part 104, the groove 113 can be stably guided toward the engaging part 66 in cooperation with the opening 102.

[Other Embodiments of Engagement Guide Part]

Although FIGS. 7 and 8 illustrate the first form in which the distal end member 30 is provided with the engagement guide part 104, the engagement guide part of the invention including the engagement guide part 104 may be provided in at least one of the distal end member 30 or the erection pedestal 58. As other forms of the engagement guide part of the invention, there are a second form in which the erection pedestal 58 is provided with an engagement guide part 104A (refer to FIGS. 12 and 13), a third form (refer to FIG. 14 and FIGS. 15, 16, and 17) in which the erection pedestal 58 is similarly provided with an engagement guide part 104B, and a fourth form (refer to FIG. 18) in which an engagement guide part 104D is provided from the distal end member 30 to the erection pedestal 58, and the like. Hereinafter, the second form or the fourth form will be described.

<Configuration of Engagement Guide Part 104A of Second Form>

Figure 13:
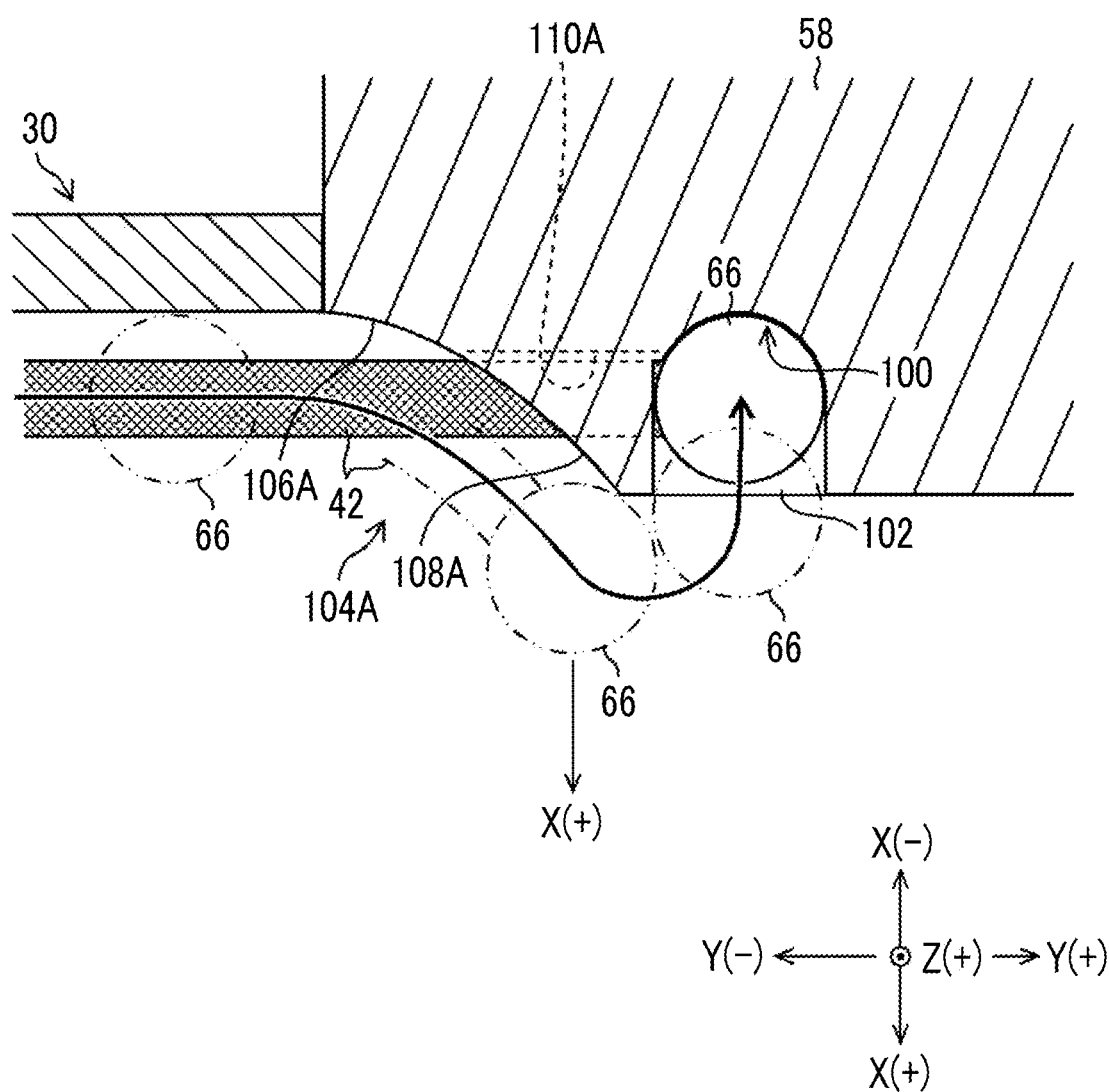
FIG. 13 is an explanatory view of the operation in which the engaging part is guided by the engagement guide part and is housed in the housing part.

FIG. 12 is an enlarged perspective view of main parts in which the engaging part 66 is housed in the housing part 100 via the engagement guide part 104A. FIG. 13 is an explanatory view sequentially illustrating the operation until the engaging part 66 is guided by an engagement guide part 104A and housed in the housing part 100.

As illustrated in FIG. 13, the engagement guide part 104A of the second form has a form in which an engagement guide path 106A and a deformation generating part 108A are provided in the erection pedestal 58. As illustrated in FIG. 12, the engagement guide path 106A is a surface that is installed consecutively with the delivery port 64 and is gradually inclined in the X(+) direction toward the Y(+) direction side. The deformation generating part 108A is formed on the Y(+) direction side that is a distal end side of the engagement guide path 106A. Additionally, the engagement guide part 104A of the second form has a form that is suitable in a case where the erection pedestal 58 is located at the erected position and the engaging part 66 is housed in the housing part 100. That is, the housing part 100 is disposed at the position that faces the delivery port 64 in a state where the erection pedestal 58 is located at the erected position. Therefore, by advancing the engaging part 66 straight from the delivery port 64, the engaging part 66 can be housed in the housing part 100 of the erection pedestal 58 located at the erected position via the engagement guide part 104A.

According to the endoscope having the engagement guide part 104A of the second form, the engaging part 66 delivered from the delivery port 64 advances while being guided to the opening 102 of the housing part 100 by the engagement guide path 106A of the erection pedestal 58. In this case, in a case where the engaging part 66 comes into contact with the deformation generating part 108A, the engaging part 66 is guided in the direction from the bottom surface of the housing part 100 toward the opening 102, that is, in the X(+) direction. Accordingly, the distal end side of the wire 42 is elastically deformed in the direction (the X(+) direction) from the bottom surface of the housing part 100 toward the opening 102. Then, in a case where the engaging part 66 that advances within the engagement guide path 106A has passed by the deformation generating part 108A, the engaging part 66 is moved in the X(−) direction by the restoring force of the wire 42, and is housed in the housing part 100 of the erection pedestal 58 via the opening 102. Additionally, in this case, the distal end side of the wire 42 is sunk in a groove 110A formed in the engagement guide part 104A.

Even in the engagement guide part 104A of the second form, since the wire 42 and the erection pedestal 58 can be coupled to each other simply by the delivery operation of the wire 42, the distal end part of the wire 42 and the erection pedestal 58 can be easily coupled to each other.

<Configuration of Engagement Guide Part 104B of Third Form>

Figure 14:
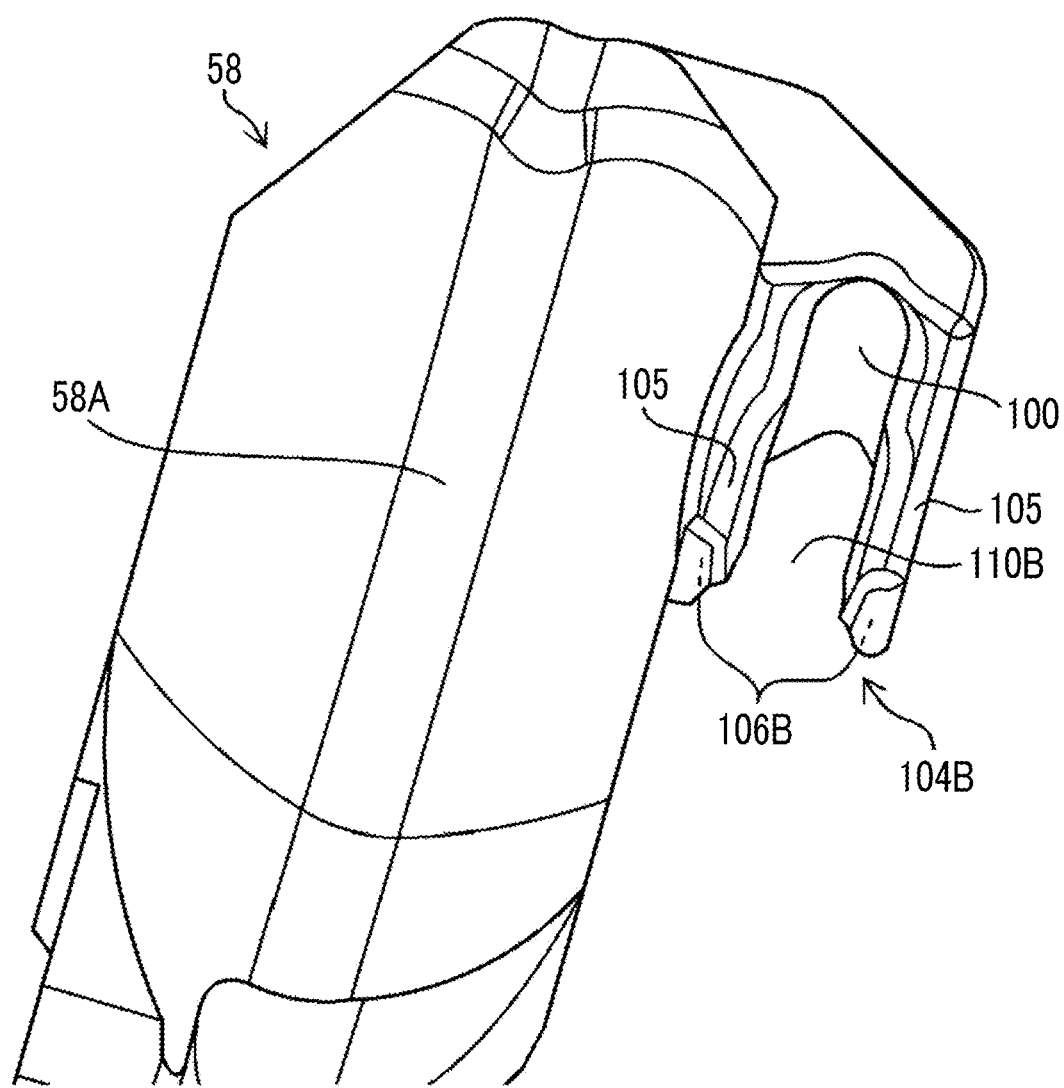
FIG. 14 is a top view of main parts of the erection pedestal comprising the engagement guide part.
Figure 15:
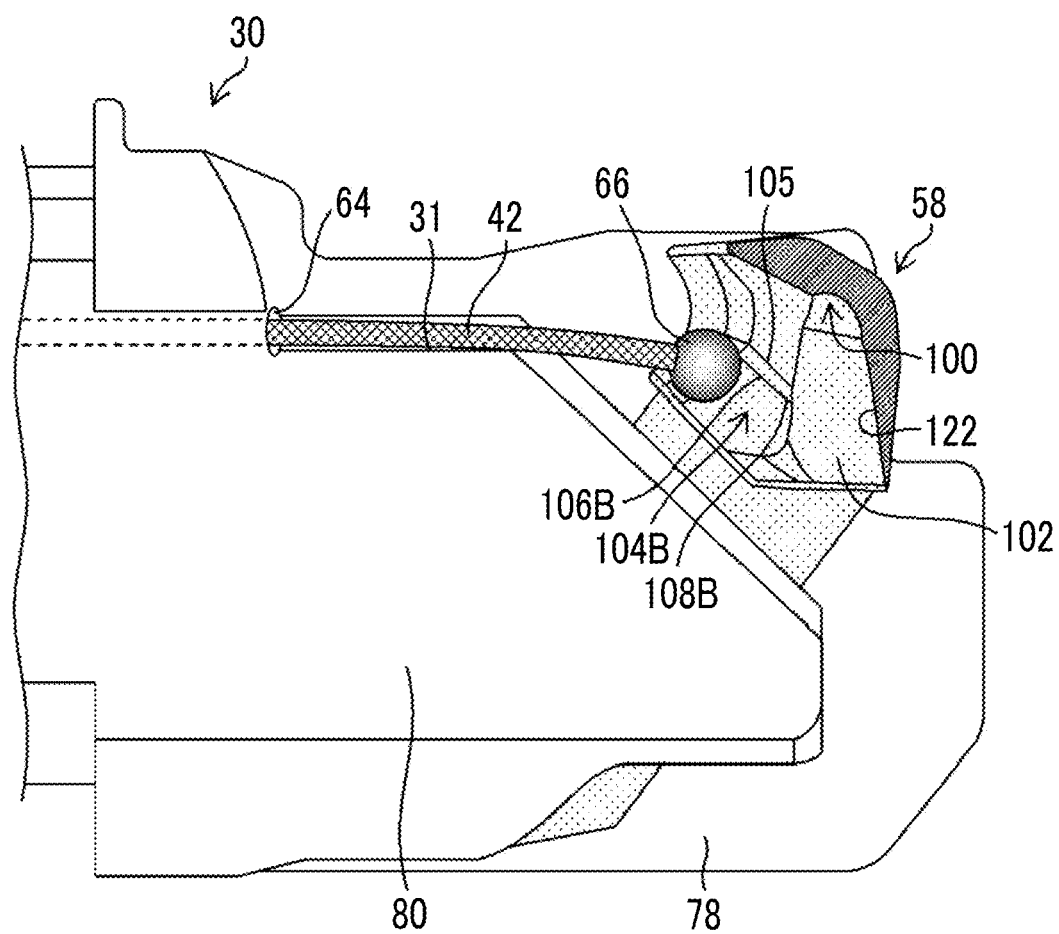
FIG. 15 is an explanatory view of the operation in which the engaging part is guided by the engagement guide part.
Figure 17:
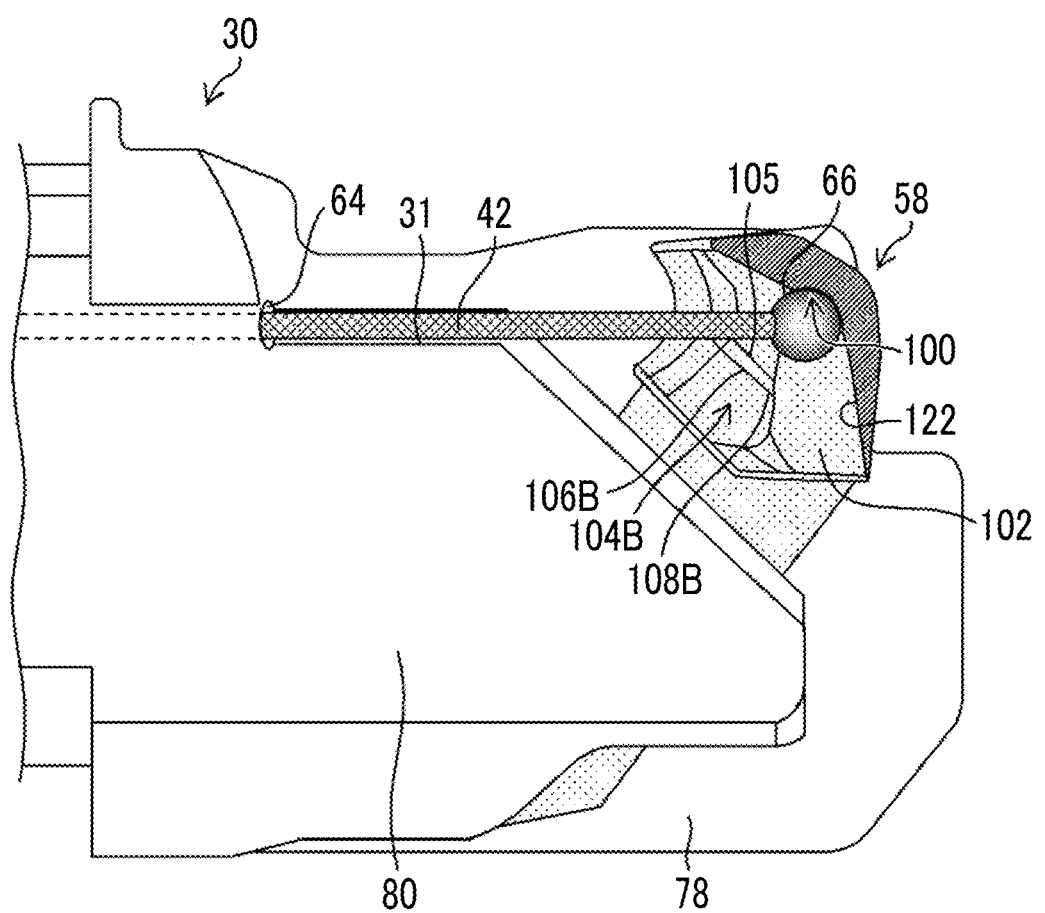
FIG. 17 is an explanatory view in which the engaging part is guided by the engagement guide part and is housed in the housing part.

FIG. 14 is a top view of main parts of the erection pedestal 58 comprising the engagement guide part 104B of the third form. FIGS. 15 and 16 are explanatory views sequentially illustrating the operation until the engaging part 66 is guided by the engagement guide part 104B and housed in the housing part 100. FIG. 17 is an explanatory view in which the engaging part 66 is guided by the engagement guide part 104B and housed in the housing part 100. In addition, FIGS. 15, 16, and 17 illustrate the housing part 100 in cross sections.

As illustrated in FIG. 14, the engagement guide part 104B of the third form has a pair of wall parts 105 and 105 that are disposed across a groove 110B in which the distal end side of the wire 42 is sunk. As illustrated in FIGS. 15, 16, and 17, an engagement guide path 106B and a deformation generating part 108B are formed in lower surfaces of the wall parts 105 and 105. Additionally, the engagement guide part 104B of the third form has a form that is suitable in a case where the erection pedestal 58 is located at the lodged position and the engaging part 66 is housed in the housing part 100. That is, the housing part 100 is disposed at the position that faces the delivery port 64 in a state where the erection pedestal 58 is located at the lodged position, and the engagement guide part 104B is disposed between the delivery port 64 and the housing part 100. Therefore, by advancing the engaging part 66 straight from the delivery port 64, the engaging part 66 can be housed in the housing part 100 of the erection pedestal 58 located at the lodged position via the engagement guide part 104B.

Additionally, as illustrated in FIG. 15, the opening 102 of the housing part 100 is formed on the Z(−) direction side of the housing part 100. Additionally, the bottom surface of the housing part 100 is formed on the Z(+) direction side of the housing part 100. Additionally, the engagement guide path 106B and the deformation generating part 108B of the engagement guide part 104B of the third form are formed to be inclined in the Z(−) direction toward the opening 102.

According to the endoscope having the engagement guide part 104B of the third form, as illustrated in FIG. 15, the engaging part 66 delivered from the delivery port 64 abuts against the engagement guide path 106B of the erection pedestal 58 located at the lodged position. Then, the engaging part 66 advances while being guided in the Y(+) direction toward the opening 102 of the housing part 100 by the engagement guide path 106B by the continued delivery operation of the wire 42. In this case, in a case where the engaging part 66 comes into contact with the deformation generating part 108B, the engaging part 66 is guided in the direction from the bottom surface of the housing part 100 toward the opening 102, that is, in the Z(−) direction. Accordingly, the distal end side of the wire 42 is elastically deformed in the direction (the Z(−) direction) from the bottom surface of the housing part 100 toward the opening 102. Then, in a case where the engaging part 66 that advances within the engagement guide path 106B has passed by the deformation generating part 108B, the engaging part 66 is moved in the Z(+) direction by the restoring force of the wire 42, and is housed in the housing part 100 of the erection pedestal 58 via the opening 102 as illustrated in FIG. 17. Additionally, in this case, the distal end side of the wire 42 is sunk in the groove 110B (refer to FIG. 14).

Even in the engagement guide part 104B of the third form, since the wire 42 and the erection pedestal 58 can be coupled to each other simply by the delivery operation of the wire 42, the distal end part of the wire 42 and the erection pedestal 58 can be easily coupled to each other.

In addition, in the endoscope comprising the engagement guide part 104B of the third form, in order to stably advance the engaging part 66 straight from the delivery port 64 to the engagement guide part 104B, it is preferable that a guide groove 31, which guides the engaging part 66 delivered from the delivery port 64 toward the engagement guide part 104B, is formed in the distal end member 30.

<Configuration of Engagement Guide Part 104D of Fourth Form>

Figure 18:
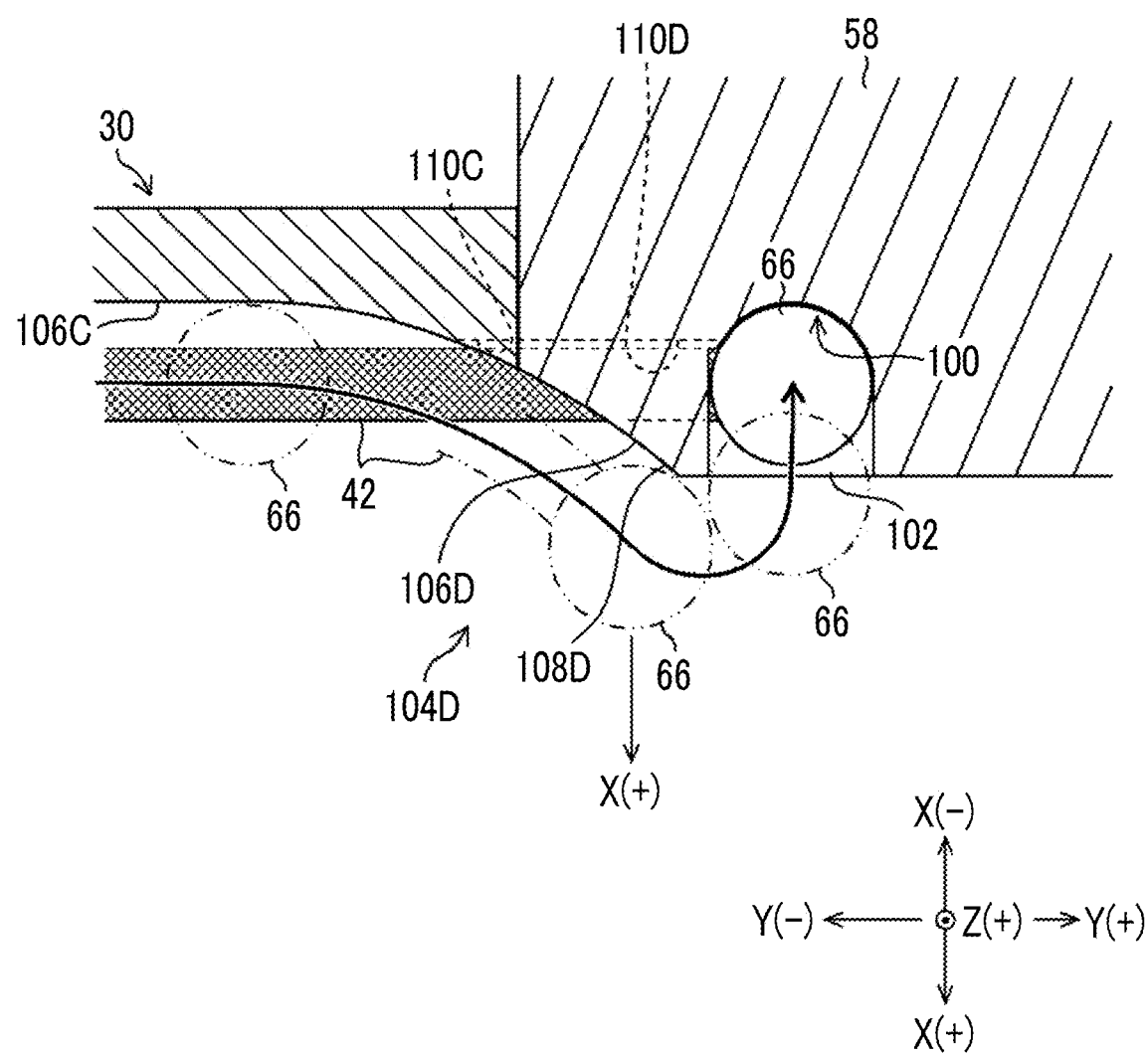
FIG. 18 is an explanatory view of the operation in which the engaging part is guided by the engagement guide part and is housed in the housing part.

FIG. 18 is an explanatory view sequentially illustrating the operation until the engaging part 66 is guided by the engagement guide part 104D and housed in the housing part 100.

The engagement guide part 104D has a first engagement guide path 106C provided in the distal end member 30, and a second engagement guide path 106D provided in the erection pedestal 58 and connected to the first engagement guide path 106C.

The first engagement guide path 106C is a surface that is curved in the X(+) direction toward the Y(+) direction side. Additionally, the second engagement guide path 106D provided in the erection pedestal 58 is a surface that is curved in the X(+) direction toward the Y(+) direction side so as to form a surface that is continuous with the first engagement guide path 106C. A deformation generating part 108D is formed on the Y(+) direction side of the second engagement guide path 106D, and is installed consecutively with the opening 102 of the housing part 100 within the second engagement guide path 106D.

Additionally, the engagement guide part 104D of the fourth form has a form that is suitable in a case where the erection pedestal 58 is located at the erected position and the engaging part 66 is housed in the housing part 100. That is, the housing part 100 is disposed at the position that faces the delivery port 64 (refer to FIG. 2) in a state where the erection pedestal 58 is located at the erected position. Therefore, by advancing the engaging part 66 straight from the delivery port 64, the engaging part 66 can be housed in the housing part 100 of the erection pedestal 58 located at the erected position via the engagement guide part 104D.

According to the endoscope having the engagement guide part 104D of the fourth form, the engaging part 66 delivered from the delivery port 64 advances while being guided toward the second engagement guide path 106D of the erection pedestal 58 by the first engagement guide path 106C of the distal end member 30. In this case, in a case where the engaging part 66 comes into contact with the deformation generating part 108D, the engaging part 66 is guided in the direction from the bottom surface of the housing part 100 toward the opening 102, that is, in the X(+) direction. Accordingly, the distal end side of the wire 42 is elastically deformed in the direction (the X(+) direction) from the bottom surface of the housing part 100 toward the opening 102. Then, in a case where the engaging part 66 that advances within the second engagement guide path 106D of the erection pedestal 58 has passed by the deformation generating part 108D of the erection pedestal 58, the engaging part 66 is moved in the X(−) direction by the restoring force of the wire 42, and is housed in the housing part 100 of the erection pedestal 58 via the opening 102. Additionally, the distal end side of the wire 42 is sunk in a groove 110C formed in the first engagement guide path 106C and a groove 110D formed in the second engagement guide path 106D.

Even in the engagement guide part 104D of the fourth form configured in this way, since the wire 42 and the erection pedestal 58 can be coupled to each other simply by the delivery operation of the wire 42, the distal end part of the wire 42 and the erection pedestal 58 can be easily coupled to each other.

In addition, the engagement guide parts 104, 104A, 104B, and 104D of the first form to the fourth form comprise the deformation generating parts 108, 108A, 108B, and 108D within the engagement guide paths 106, 106A, 106B, and 106D. Accordingly, the engaging part 66 is housed in the housing part 100 by utilizing the restoring force of the wire 42. However, the engaging part 66 may be housed in the housing part 100 via the opening 102 by being advanced along the engagement guide paths 106, 106A, 106B, 106C, and 106D without comprising the deformation generating parts 108, 108A, 108B, and 108D. In this case, the engagement guide paths 106, 106A, 106B, 106C, and 106D function as an engagement guide part of the invention.

<Configuration of Engagement Guide Part 104E of Fifth Form>

FIG. 19 is an enlarged perspective view in which the engaging part 66 is housed in the housing part 100 via an engagement guide part 104E of a fifth form. FIG. 20 is an explanatory view sequentially illustrating the operation until the engaging part 66 is guided by the engagement guide part 104E and housed in the housing part 100.

As illustrated in FIGS. 19 and 20, the engagement guide part 104E has an engagement guide path 106E that guides the engaging part 66 delivered from the delivery port 64 (refer to FIG. 2), to the opening 102.

The engagement guide path 106E is formed in the distal end member 30, and comprises a first engagement guide path 106F that is curved in the X(+) direction toward the opening 102, and a second engagement guide path 106G that is formed in the erection pedestal 58 and connected to the first engagement guide path 106F. Additionally, the second engagement guide path 106G is formed in the Y(+)-Y(−) direction in a case where the erection pedestal 58 is located at the erected position.

A deformation generating part 108F is provided at an end part within the first engagement guide path 106F on the second engagement guide path 106G side. Here, in a case where a direction, which extends perpendicularly from the opening surface 103 of the opening 102 toward the outside of the opening 102, is defined as a first direction (X(+)), the deformation generating part 108F comes into contact with the engaging part 66 that advances toward the second engagement guide path 106G within the first engagement guide path 106F, and displaces the engaging part 66 in the first direction (X(+)). Accordingly, the wire 42 is elastically deformed in the first direction (X(+)). The elastic deformation of the wire 42 is maintained while the engaging part 66 passes through the second engagement guide path 106G. Accordingly, in a case where the engaging part 66 has reached the opening 102, the engaging part 66 is moved in the X(−) direction by the restoring force of the wire 42, and is housed in the housing part 100 from the opening 102.

According to the endoscope having the engagement guide part 104E of the fifth form, the engaging part 66 delivered from the delivery port 64 advances while being guided toward the erection pedestal 58 by the first engagement guide path 106F of the distal end member 30. Then, in a case where the engaging part 66 comes into contact with the deformation generating part 108F within the first engagement guide path 106F, the engaging part 66 is displaced in the first direction (X(+)), and the wire 42 is elastically deformed in the first direction (X(+)). Then, the engaging part 66 that has passed through the first engagement guide path 106F advances along the second engagement guide path 106G. In this case, the wire 42 maintains the elastic deformation. Then, in a case where the engaging part 66 has reached the opening 102, the engaging part 66 is moved in the X(−) direction by the restoring force of the wire 42, and is housed in the housing part 100 from the opening 102. Additionally, the distal end side of the wire 42 is sunk in a groove 110F formed in the first engagement guide path 106F and a groove 110G formed in the second engagement guide path 106G.

Even in the engagement guide part 104E of the fifth form, since the wire 42 and the erection pedestal 58 can be coupled to each other simply by the delivery operation of the wire 42, the distal end part of the wire 42 and the erection pedestal 58 can be easily coupled to each other.

Figure 21:
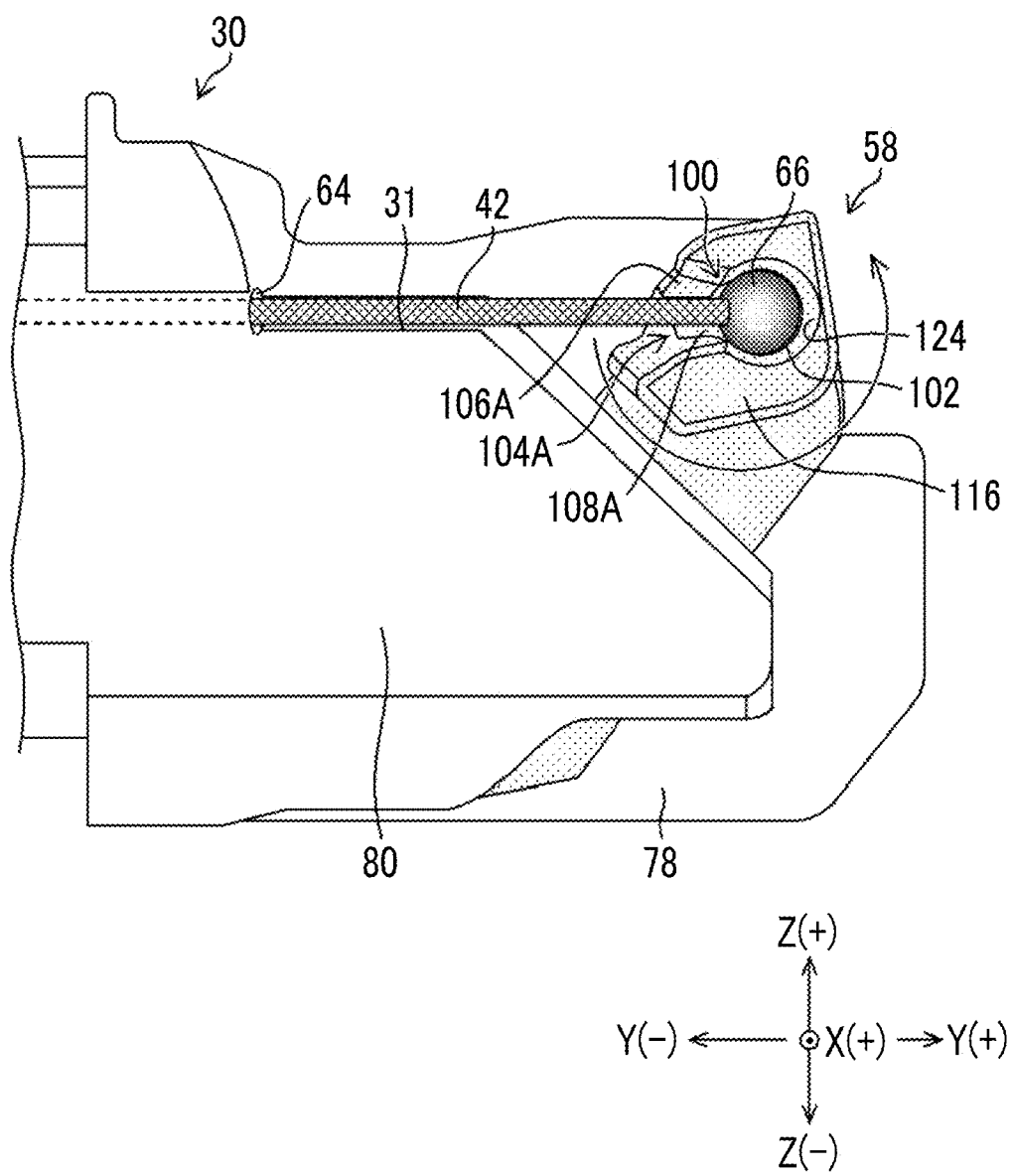
FIG. 21 is a side view of the distal end part in which a coupling part in which the housing part is formed is made rotationally movable at the erection pedestal.
Figure 22:
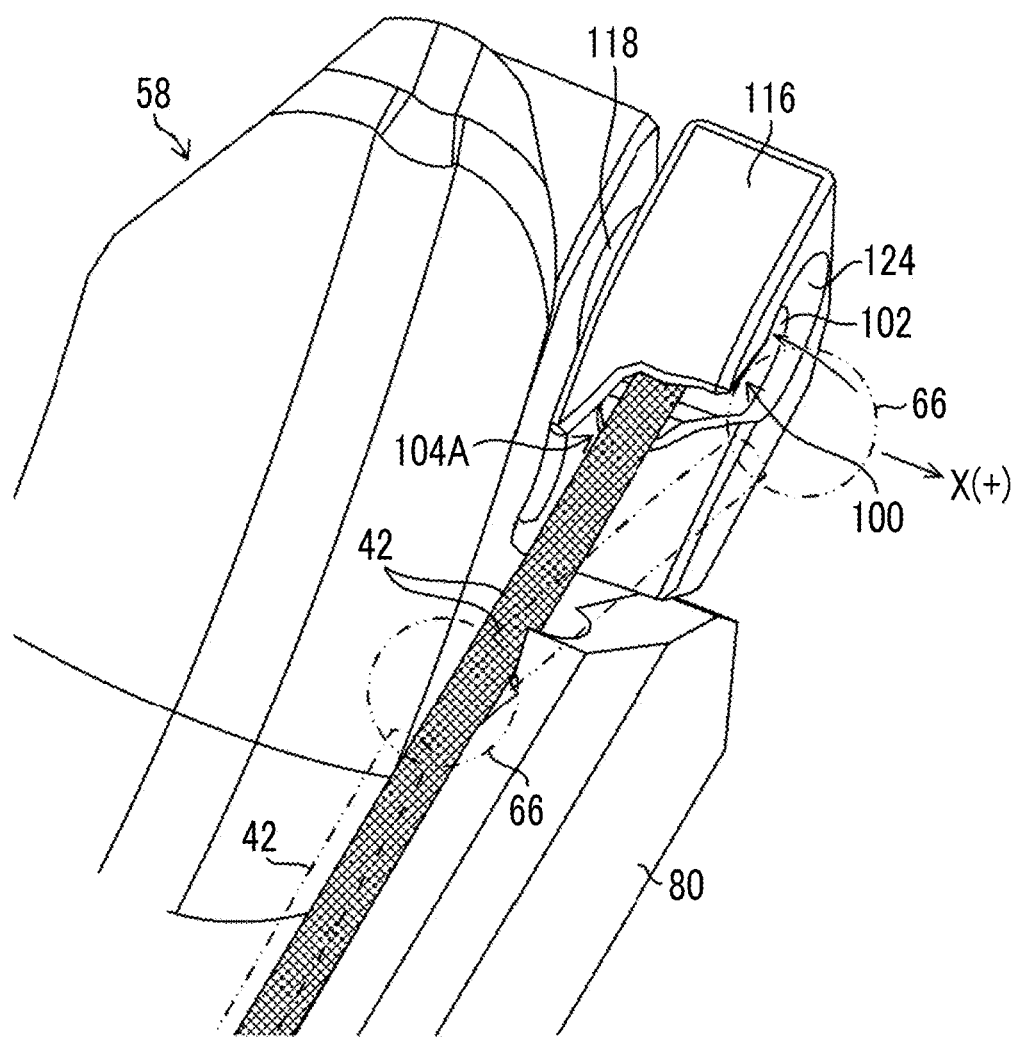
FIG. 22 is a top view of FIG. 21.

FIG. 21 is a side view of the distal end part 28 illustrating another form in which a coupling part 116 in which the housing part 100 is formed is provided in a rotationally movable manner on a right side surface of the erection pedestal 58. FIG. 22 is a top view of FIG. 21, and is an explanatory view sequentially illustrating the operation until the engaging part 66 is housed in the housing part 100.

The form illustrated in FIG. 21 is a form in which a stress is not applied to the wire 42 in a case where the erection pedestal 58 is erected from the lodged position to the erected position. Additionally, the form illustrated in FIG. 21 is a form that is suitable in a case where the erection pedestal 58 is located at the lodged position and the engaging part 66 is housed in the housing part 100. That is, the housing part 100 is disposed at the position that faces the delivery port 64 in a state where the erection pedestal 58 is located at the lodged position. Accordingly, by advancing the engaging part 66 straight from the delivery port 64, the engaging part 66 can be housed in the housing part 100 of the erection pedestal 58 located at the lodged position.

According to FIG. 21, a right side surface of the erection pedestal 58 is provided with the coupling part 116 in which the housing part 100 is formed. The coupling part 116 is coupled to the erection pedestal 58 in a rotationally movable manner about a shaft 118 (refer to FIG. 22) parallel to axes (refer to FIG. 6) of the rotational movement shafts 84 and 86 of the erection pedestal 58 such that a stress is not applied to the wire 42 in a case where the erection pedestal 58 is erected from the lodged position to the erected position.

The coupling part 116 is coupled to the erection pedestal 58 in a rotationally movable manner by the shaft 118. However, in a case where the engaging part 66 is housed in the housing part 100, as illustrated in FIG. 21, the housing part 100 is held at the position facing the delivery port 64 by a holding part (not illustrated) so as not to be rotationally moved. The holding part is provided in a protecting member (not illustrated) to be mounted on the distal end member 30 as an example. Accordingly, in a case where the protecting member is mounted on the distal end member 30, the housing part 100 is held at the position that faces the delivery port 64.

Additionally, the engagement guide part 104A illustrated in FIGS. 12 and 13 is formed in the coupling part 116. Accordingly, the engaging part 66 that has passed the distal end member 30 is housed in the housing part 100 via the engagement guide path 106A by the continued pushing operation of the wire 42.

Meanwhile, in a case where the coupling part 116 is fixed to the erection pedestal 58, there is a case where the erection operational feeling of the erection lever 22 becomes heavy. That is, as illustrated in FIG. 21, in a case where the pulling operation of the wire 42 is performed and the erection pedestal 58 is moved from the lodged position to the erected position after the engaging part 66 is housed in the housing part 100 of the erection pedestal 58, the wire 42 also moves along a circular-arc drawn by the engaging part 66 as the erection pedestal 58 moves to the erected position. In this case, since stress is applied to the wire 42 from the engaging part 66 to the engagement guide part 104A, there is a concern that the erection operational feeling becomes heavy or damage is given to the wire 42.

In the form illustrated in FIG. 21, since the coupling part 116 is coupled to the erection pedestal 58 in a rotationally movable manner about the shaft 118, the coupling part 116 rotates as the erection pedestal 58 moves from the lodged position to the erected position. Accordingly, since the linear shape of the wire 42 between the engaging part 66 and a delivery port 64 is maintained, it is possible to prevent the wire 42 from being stressed. Hence, in the form illustrated in FIG. 21, the erection operational feeling does not become heavy or damage is not given to the wire 42.

[Detachment Structure of Wire 42]

Next, a structure for detaching the engaging part 66 of the wire 42 housed in the housing part 100 of the erection pedestal 58 from the housing part 100 will be described.

<Detachment Structure of First Form>

Figure 23:
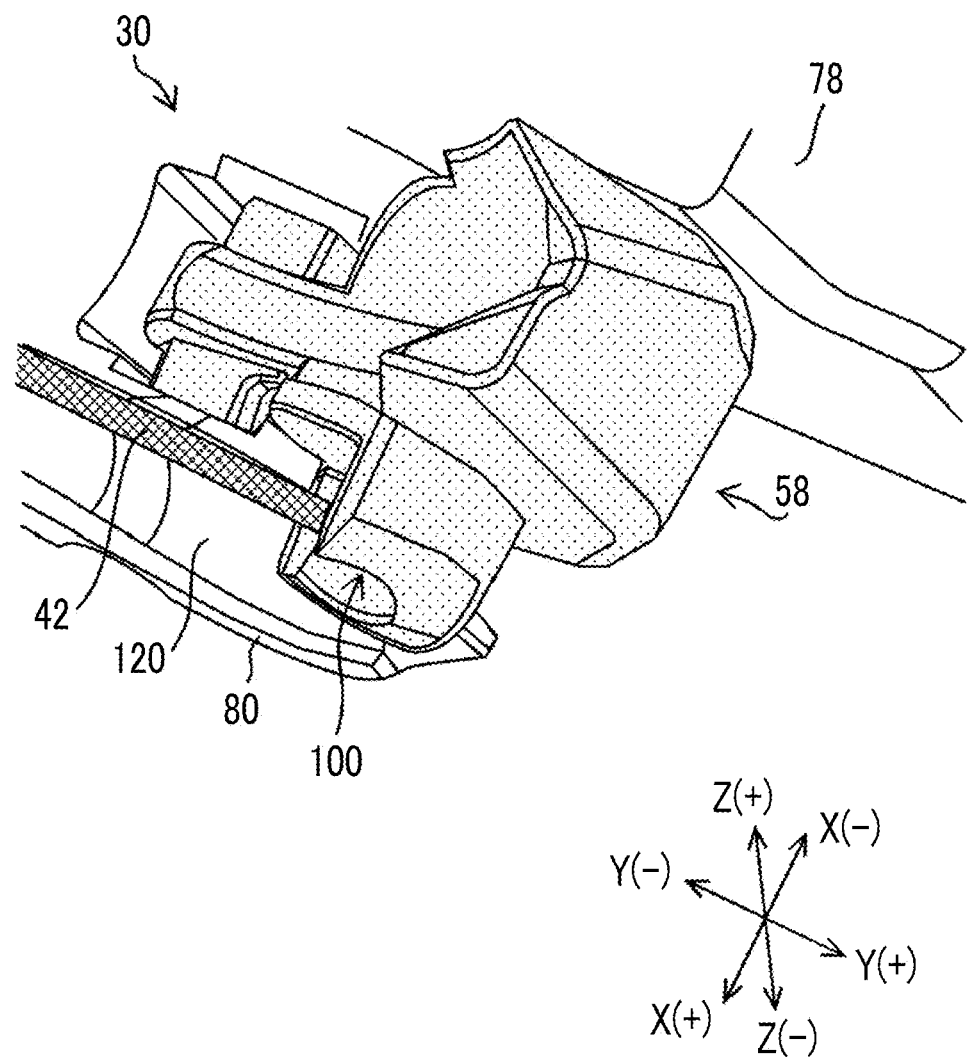
FIG. 23 is a top view of the distal end member where the erection pedestal is located at the erected position.
Figure 24:
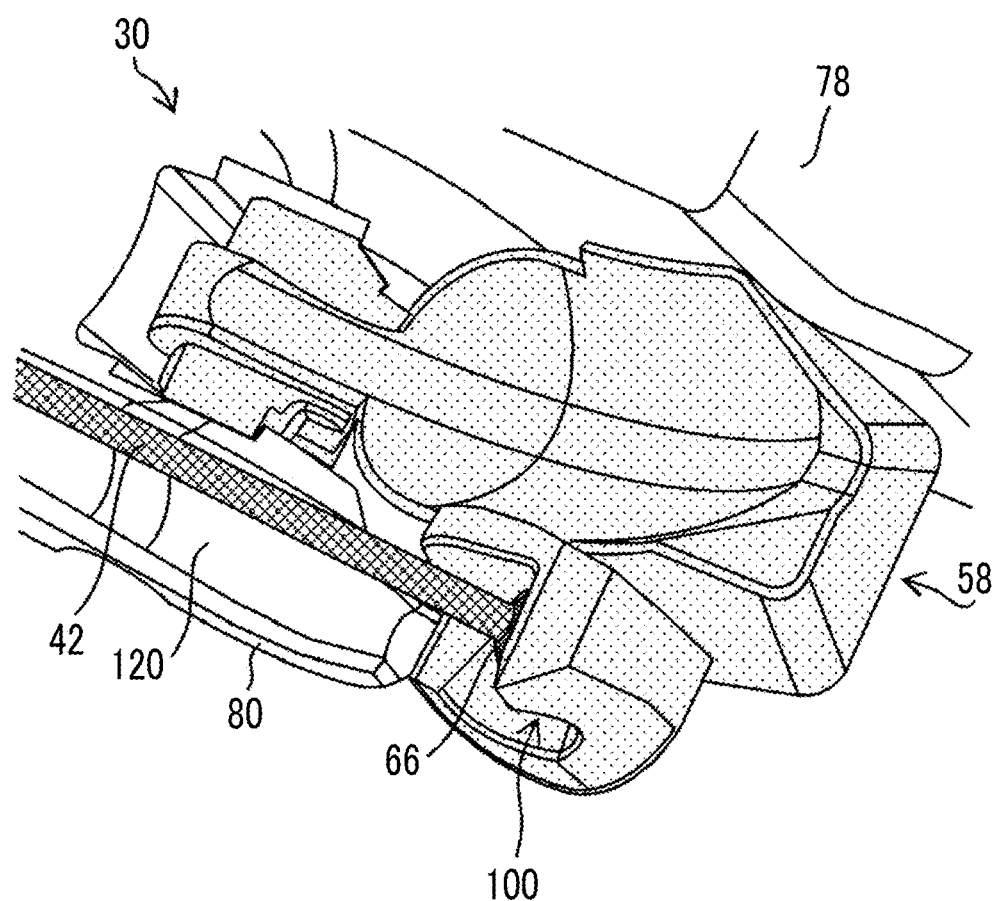
FIG. 24 is a top view of the distal end member where the erection pedestal is located at the lodged position.
Figure 25:
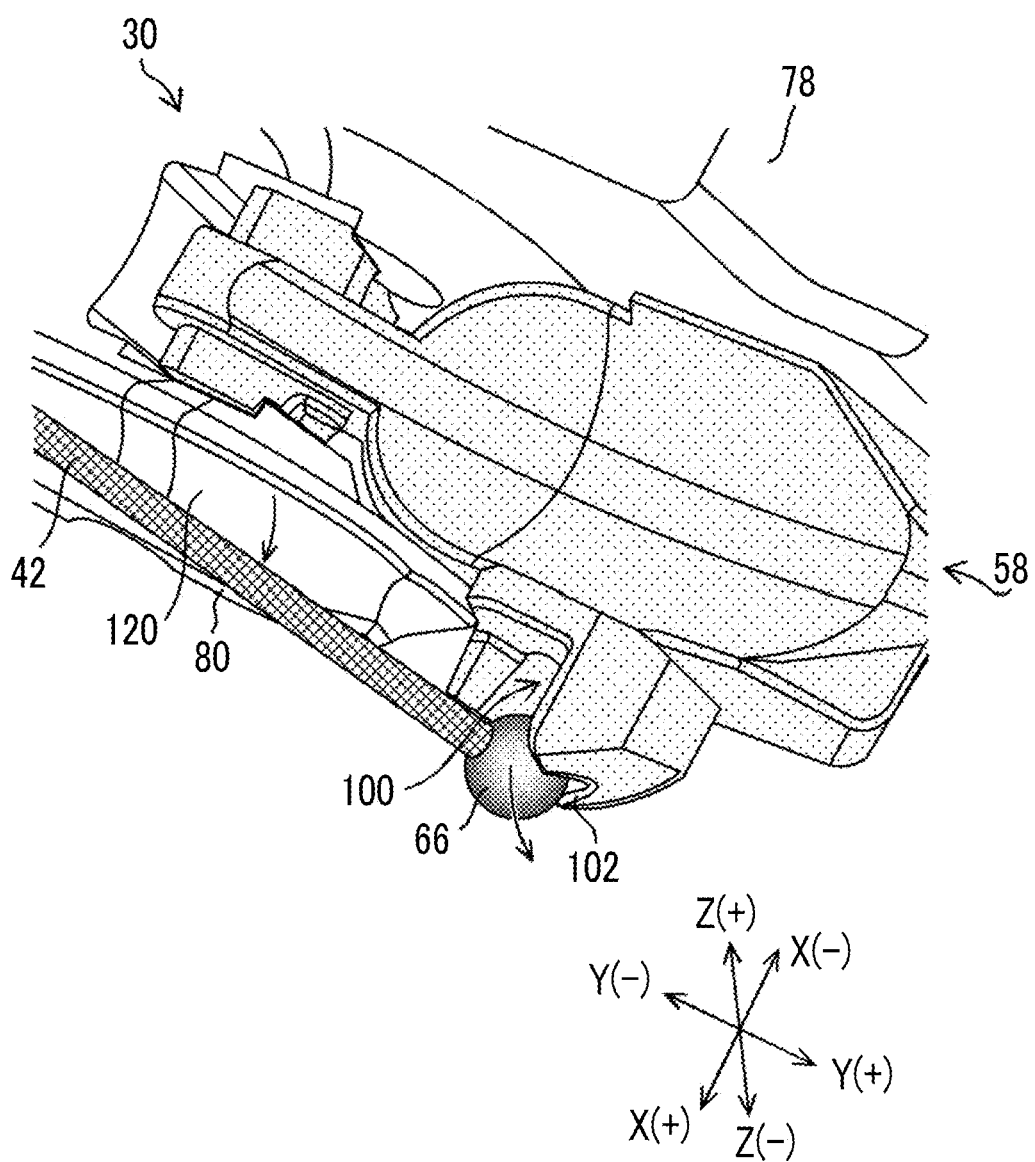
FIG. 25 is a top view of the distal end member in a state where the engaging part is detached from the housing part.

As illustrated in top views of the distal end member 30 illustrating in FIGS. 23, 24, and 25, a detachment structure of the first form is a form in which the distal end member 30 is provided with a separation guide surface 120. Additionally, FIG. 23 is a top view of the distal end member 30 in which the erection pedestal 58 below is located at the erected position, FIG. 24 is a top view of the distal end member 30 in which the erection pedestal 58 is located at the lodged position, and FIG. 25 is a top view of the distal end member 30 in a state which the engaging part 66 is detached from the housing part 100.

The separation guide surface 120 is provided on an upper surface, on the Z(+) direction side, of the partition wall 80 disposed on the X(+) direction side of the distal end member 30 (refer to FIG. 2). The separation guide surface 120 is a guide surface (refer to FIGS. 2 and 3) that is inclined in the Z(−) direction toward the X(+) direction side of the distal end member 30. Additionally, the separation guide surface 120 functions as a surface of guiding the wire 42 in a direction in which the engaging part 66 is separated from the inside of the housing part 100 to the outside of the opening 102 in a case where a further pushing operation of the wire 42 in a state where the engaging part 66 is housed in the housing part 100 and the erection pedestal 58 is located at the lodged position.

<Wire Detaching Method by Detachment Structure of First Form>

According to the wire detaching method of the first form, first, the cover 74 illustrated in FIG. 4 is detached from the operating part 24, and the proximal end engaging part 72 of the wire 42 is detached from the exposed distal end engaging part 70 of the drive shaft 68. Next, the wire 42 is operated to be pushed from the introduction port 62 of the operating part 24, and the erection pedestal 58 is located from the erected position of FIG. 23 to the lodged position of FIG. 24. Thereafter, in a case where the wire 42 is operated to be further pushed, the wire 42 is guided in the X(+) direction in which the engaging part 66 is separated from the inside of the housing part 100 to the outside the opening 102 by the separation guide surface 120 of the distal end member 30. Accordingly, as illustrated in FIG. 25, the engaging part 66 is easily separated from the inside of the housing part 100 to the outside of the opening 102 by the restoring force of the wire 42.

As described above, according to the wire detaching method of the first form in which the separation guide surface 120 is formed in the distal end member 30, the engaging part 66 can be separated from the housing part 100 by the pushing operation of the wire 42. Thus, the distal end part of the wire 42 can be easily detached from the erection pedestal 58.

Contrary to the pushing operation of the wire 42, in the case of a structure in which the engaging part 66 is separated from the housing part 100 by the pulling operating of the wire 42, there is a concern that the engaging part 66 is erroneously separated from the housing part 100 by a large force of pulling the wire 42 in order to change the delivery direction of a treatment tool at the time of examination. In contrast, the force of pushing the wire 42 in order to locate the erection pedestal 58 at the lodged position is smaller than the force of pulling the wire 42. Therefore, as in the detachment structure of the first form, it is more preferable to separate the engaging part 66 from the housing part 100 by the pushing operation of the wire 42 because the engaging part 66 is not erroneously separated from the housing part 100.

In addition, the operation of locating the erection pedestal 58 at the lodged position of FIG. 24 may be executed by performing the rotational movement operation of the erection lever 22 without detaching the proximal end engaging part 72 of the wire 42 from the distal end engaging part 70 of the drive shaft 68.

Thereafter, the wire 42 is extracted from the delivery port 64. The wire 42 can also be extracted from the introduction port 62 in a proximal end direction (refer to FIG. 4). However, since body fluids, such as blood, have adhered to the engaging part 66 after the examination, the wire 42 is extracted in a distal end direction from the delivery port 64 side. Accordingly, it is possible to prevent that the body fluids are drawn into the inside of the wire insertion channel 44 (refer to FIG. 2) or the body fluids are splashed and scattered in a case where the engaging part 66 comes out from the introduction port 62. Then, the wire 42 is extracted from the delivery port 64, and then the wire insertion channel 44 that becomes empty is cleaned and disinfected. Accordingly, the cleaning performance of the wire insertion channel 44 that has a fine diameter is improved. In addition, in a case where a new wire 42 and the erection pedestal are coupled to each other after the cleaning of the endoscope, the wire attaching method illustrated in FIG. 9 or 10 is executed.

<Detachment Structure of Second Form>

As illustrated in FIG. 17, a detachment structure of the second form is a form in which the housing part 100 of the erection pedestal 58 is provided with a separation guide surface 122.

The separation guide surface 122 of the housing part 100 illustrated in FIG. 17 is formed as a guide surface that is gradually inclined in the Y(+) direction toward the Z(−) direction side. Additionally, the separation guide surface 122 functions as a surface of guiding the engaging part 66 in a direction in which the engaging part 66 is separated from the inside of the housing part 100 to the outside of the opening 102 in a case where a further pushing operation of the wire 42 in a state where the engaging part 66 is housed in the housing part 100 and the erection pedestal 58 is located at the lodged position.

<Wire Detaching Method by Detachment Structure of Second Form>

Figure 26:
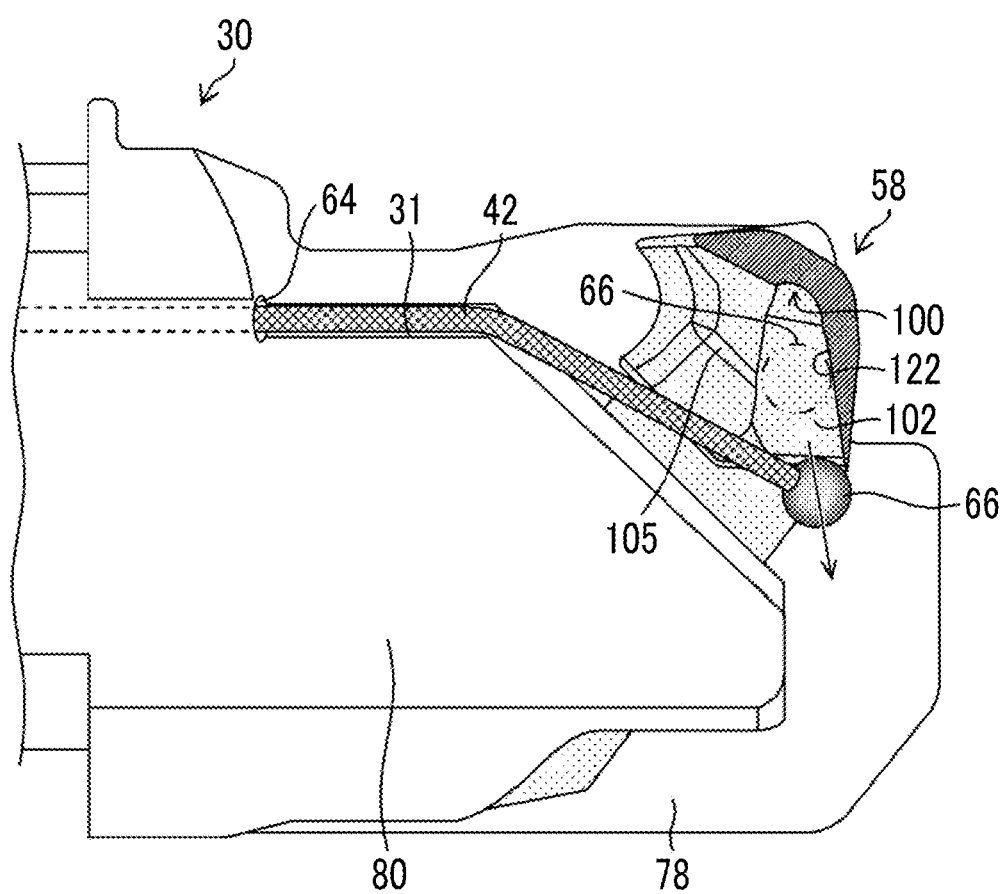
FIG. 26 is an explanatory view of the operation of a first form in which a wire is detached by a separation guide surface of the housing part.

According to the wire detaching method of a second form, first, the cover 74 illustrated in FIG. 4 is detached from the operating part 24, and the proximal end engaging part 72 of the wire 42 is detached from the exposed distal end engaging part 70 of the drive shaft 68. Next, the wire 42 is operated to be pushed from the introduction port 62 of the operating part 24, and the erection pedestal 58 is located at the lodged position as illustrated in FIG. 17. Thereafter, in a case where the wire 42 is operated to be further pushed, the engaging part 66 is guided in the direction in which the engaging part 66 is separated from the inside of the housing part 100 to the outside the opening 102 by the separation guide surface 122 of the housing part 100. Accordingly, as illustrated in FIG. 26, the engaging part 66 is easily separated from the inside of the housing part 100 to the outside of the opening 102.

<Detachment Structure of Third Form>

As illustrated in FIG. 21, a detachment structure of a third form is a form in which the housing part 100 of the erection pedestal 58 is provided with a separation guide surface 124.

The separation guide surface 124 of the housing part 100 illustrated in FIG. 21 is formed as a guide surface that is gradually inclined in the Y(+) direction toward the X(+) direction side of the distal end member 30. Additionally, the separation guide surface 124 functions as a surface of guiding the engaging part 66 in a direction in which the engaging part 66 is separated from the inside of the housing part 100 to the outside of the opening 102 in a case where a further pushing operation of the wire 42 in a state where the engaging part 66 is housed in the housing part 100 and the erection pedestal 58 is located at the lodged position.

<Wire Detaching Method by Detachment Structure of Third Form>

Figure 27:
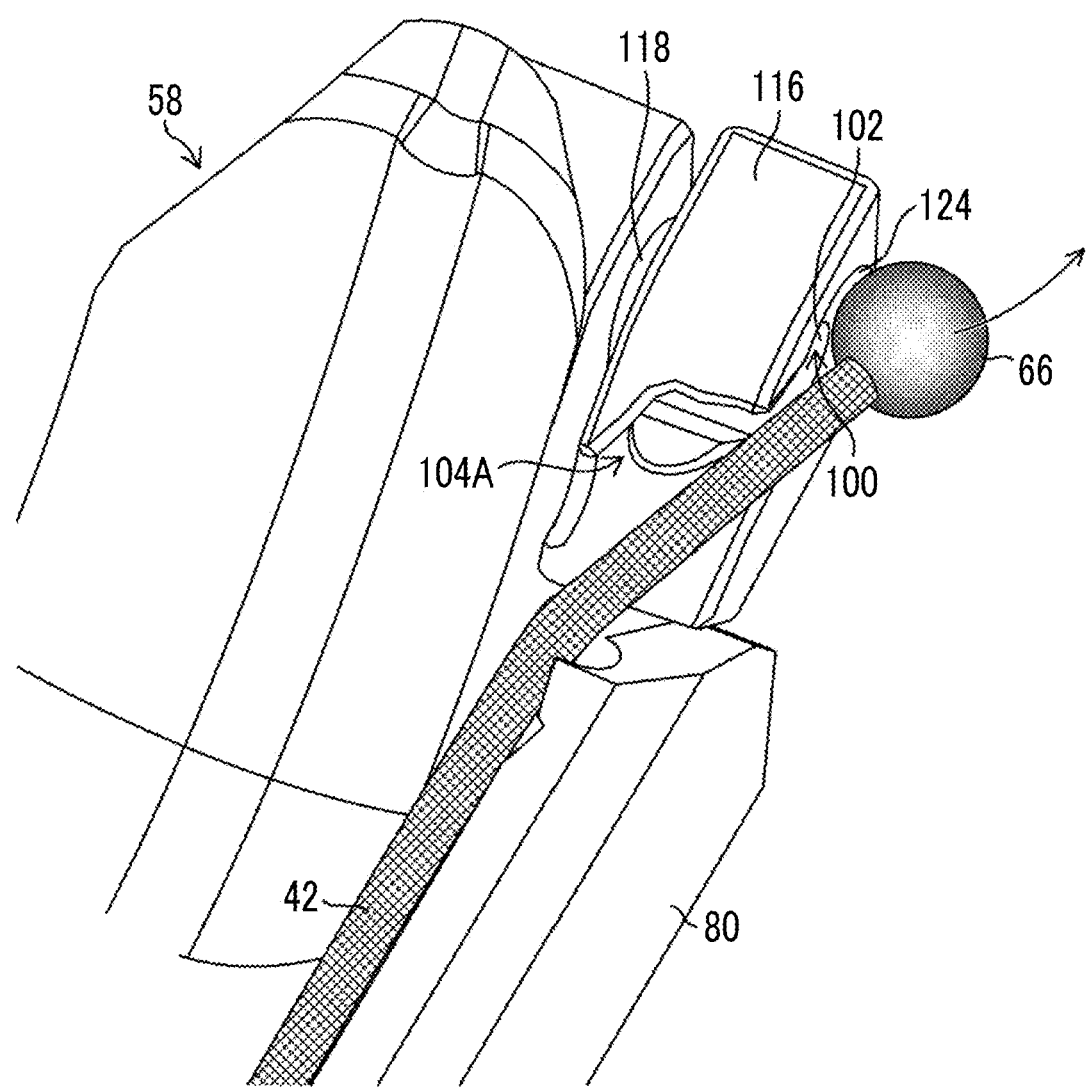
FIG. 27 is an explanatory view of the operation of a second form in which the wire is detached by the separation guide surface of the housing part.

According to the wire detaching method of the third form, first, the cover 74 illustrated in FIG. 4 is detached from the operating part 24, and the proximal end engaging part 72 of the wire 42 is detached from the exposed distal end engaging part 70 of the drive shaft 68. Next, the wire 42 is operated to be pushed from the introduction port 62 of the operating part 24, and the erection pedestal 58 is located at the lodged position as illustrated in FIG. 21. Thereafter, in a case where the wire 42 is operated to be further pushed, the engaging part 66 is guided in the direction in which the engaging part 66 is separated from the inside of the housing part 100 to the outside the opening 102 by the separation guide surface 124 of the housing part 100. Accordingly, as illustrated in FIG. 27, the engaging part 66 is easily separated from the inside of the housing part 100 to the outside of the opening 102.

As described above, even in the wire detaching methods of the second form and the third form in which the separation guide surface 122 and the separation guide surface 124 are formed in the housing part 100, the engaging part 66 can be separated from the housing part 100 by the pushing operation of the wire 42. Thus, the distal end part of the wire 42 can be easily detached from the erection pedestal 58.

In the above embodiment, the duodenum mirror has been exemplified and described as the endoscope 10. However, as long as an endoscope comprising an erection pedestal for adjusting the delivery direction of a treatment tool at a distal end part of an insertion part is provided, the invention can be applied to various endoscopes, such as an ultrasonic endoscope.

EXPLANATION OF REFERENCES

- 10: endoscope
- 12: endoscope system
- 14: treatment tool
- 14A: cup
- 16: processor device
- 18: light source device
- 20: display
- 22: erection lever
- 24: operating part
- 26: insertion part
- 28: distal end part
- 30: distal end member
- 30A: peripheral surface
- 31: guide groove
- 32: universal cord
- 34: connector
- 35: connector
- 36: bending part
- 38: flexible part
- 40: treatment tool insertion channel
- 42: wire
- 44: wire insertion channel
- 46: angle knob
- 48: air/water supply button
- 50: suction button
- 52: air/water supply nozzle
- 54: treatment tool introduction port
- 56: treatment tool delivery port
- 58: erection pedestal
- 58A: guide surface
- 58B: base part
- 60: recess
- 60A: wall surface
- 62: introduction port
- 64: delivery port
- 66: engaging part
- 68: drive shaft
- 70: distal end engaging part
- 72: proximal end engaging part
- 74: cover
- 76: cap
- 76A: opening window
- 78: partition wall
- 78A: bearing part
- 80: partition wall
- 80A: bearing part
- 82: erection pedestal housing chamber
- 84: rotational movement shaft
- 86: rotational movement shaft
- 88: optical system housing chamber
- 90: illumination window
- 92: observation window
- 100: housing part
- 102: opening
- 103: opening surface
- 104: engagement guide part
- 104A: engagement guide part
- 104B: engagement guide part
- 104D: engagement guide part
- 104E: engagement guide part
- 105: wall part
- 106: engagement guide path
- 106A: engagement guide path
- 106B: engagement guide path
- 106C: first engagement guide path
- 106D: second engagement guide path
- 106E: engagement guide path
- 106F: first engagement guide path
- 106G: second engagement guide path
- 108: deformation generating part
- 108A: deformation generating part
- 108B: deformation generating part
- 108D: deformation generating part
- 108F: deformation generating part
- 110: groove
- 111: groove
- 110A: groove
- 110B: groove
- 110C: groove
- 110D: groove
- 110F: groove
- 110G: groove
- 112: protecting member
- 113: groove
- 114: holding part
- 116: coupling part
- 118: shaft
- 120: separation guide surface
- 122: separation guide surface
- 124: separation guide surface

What is claimed is:

1. An endoscope comprising:
a proximal operating part including an operating member;
an insertion part having a proximal end part connected to the proximal operating part;
a distal end member that is provided at a distal end part of the insertion part;
a treatment tool erection pedestal that is attached to the distal end member and is rotationally movable between an erected position and a lodged position;
a wire that is coupled to the treatment tool erection pedestal on a distal end side thereof, is coupled to the operating member on a proximal end side thereof, and is pushed and pulled depending on an operation of the operating member, thereby rotationally moving the treatment tool erection pedestal;

an engaging part that is provided at a distal end part of the wire;

a housing part that is provided in the treatment tool erection pedestal and is formed with an opening for housing the engaging part;

an introduction port that is provided in the proximal operating part and allows the wire to be introduced thereinto with the engaging part as a head;

a delivery port that is provided in the distal end member and allows the wire to be delivered therefrom with the engaging part as a head;

a wire insertion channel that is provided inside the insertion part and communicates the introduction port with the delivery port; and an engagement guide part that is installed adjacent to the housing part, is provided in at least one of the distal end member or the treatment tool erection pedestal, wherein the engagement guide part includes an engagement guide path that guides the engaging part delivered from the delivery port, to the opening of the housing part.

2. The endoscope according to claim 1,
wherein the engagement guide path guides the engaging part delivered from the delivery port, to the opening of the housing part in a direction from the delivery port toward the housing part, and the engagement guide part includes a deformation generating part that is installed adjacent to the opening of the housing part inside the engagement guide path and comes into contact with the engaging part that advances toward the opening inside the engagement guide path to elastically deform the wire in a direction in which the engaging part goes from a bottom surface of the housing part toward the opening, and wherein the engaging part that advances within the engagement guide path is housed in the housing part from the opening by a restoring force of the wire in a case where the engaging part has passed by the deformation generating part.

3. The endoscope according to claim 2,
wherein the engagement guide path and the deformation generating part are provided in the distal end member.

4. The endoscope according to claim 3,
wherein the engaging part is a spherical body, and the housing part is a spherical recess that houses the engaging part that is the spherical body.

5. The endoscope according to claim 2,
wherein the engagement guide path and the deformation generating part are provided in the treatment tool erection pedestal.

6. The endoscope according to claim 5,
wherein the engaging part is a spherical body, and the housing part is a spherical recess that houses the engaging part that is the spherical body.

7. The endoscope according to claim 2,
wherein the engagement guide path has a first engagement guide path provided in the distal end member, and a second engagement guide path that is provided in the treatment tool erection pedestal and is connected to the first engagement guide path, and wherein the deformation generating part is installed adjacent to the opening of the housing part within the second engagement guide path.

8. The endoscope according to claim 7,
wherein the engaging part is a spherical body, and the housing part is a spherical recess that houses the engaging part that is the spherical body.

9. The endoscope according to claim 2,
wherein the engaging part is a spherical body, and the housing part is a spherical recess that houses the engaging part that is the spherical body.

10. The endoscope according to claim 1,
wherein the an engagement guide path guides the engaging part delivered from the delivery port, to the opening of the housing part, and includes a first engagement guide path provided in the distal end member and a second engagement guide path is provided in the treatment tool erection pedestal and connected to the first engagement guide path, and the engagement guide part includes a deformation generating part that is provided at an end part within the first engagement guide path on the second engagement guide path side and, in a case where a direction that extends perpendicularly from an opening surface of the opening toward an outside of the opening is defined as a first direction, comes into contact the engaging part, which advances toward the second engagement guide path inside the first engagement guide path, to displace the engaging part in the first direction, thereby elastically deforming the wire, wherein the second engagement guide path comes into contact with the engaging part, which advances toward the opening, and maintains the elastic deformation of the wire, and wherein the engaging part is housed in the housing part from the opening by a restoring force of the wire in a case where the engaging part has reached the opening.

11. The endoscope according to claim 1,
wherein the engaging part is a spherical body, and the housing part is a spherical recess that houses the engaging part that is the spherical body.

12. The endoscope according to claim 1,
wherein the distal end member is provided with a separation guide surface, which guides the wire in a direction in which the engaging part is separated from an inside of the housing part to the outside of the opening in a case where the wire is operated to be further pushed in a state where the engaging part is housed in the housing part and the treatment tool erection pedestal is located in the lodged position.

13. The endoscope according to claim 1,
wherein a separation guide surface, which guides the engaging part in a direction in which the engaging part is separated from an inside of the housing part to the outside of the opening in a case where the wire is operated to be further pushed in a state where the engaging part is housed in the housing part and the treatment tool erection pedestal is located in the lodged position, is formed in the housing part.

14. The endoscope according to claim 1,
wherein the housing part is disposed at a position that faces the delivery port in a state where the treatment tool erection pedestal is located at the erected position.

15. The endoscope according to claim 1,
wherein the housing part is disposed at a position that faces the delivery port in a state where the treatment tool erection pedestal is located at the lodged position.

16. The endoscope according to claim 1,
wherein the treatment tool erection pedestal is provided with a coupling part in which the housing part is formed, and
wherein the coupling part is coupled to the treatment tool erection pedestal in a rotationally movable manner about a shaft parallel to a rotational movement shaft of the treatment tool erection pedestal.

\* \* \* \* \*